(12) United States Patent
Kong et al.

(10) Patent No.: US 11,717,542 B2
(45) Date of Patent: Aug. 8, 2023

(54) **USING TUMOR-NAVIGATING *SALMONELLA* TO MODULATE TUMOR METABOLISM**

(71) Applicant: ARIZONA BOARD OF REGENTS ON BEHALF OF ARIZONA STATE UNIVERSITY, Scottsdale, AZ (US)

(72) Inventors: Wei Kong, Phoenix, AZ (US); Lingchen Fu, Tempe, AZ (US); Yixin Shi, Phoenix, AZ (US); Bo Ning, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 17/433,225

(22) PCT Filed: Feb. 20, 2020

(86) PCT No.: PCT/US2020/019110
§ 371 (c)(1),
(2) Date: Aug. 23, 2021

(87) PCT Pub. No.: WO2020/172461
PCT Pub. Date: Aug. 27, 2020

(65) Prior Publication Data
US 2021/0386795 A1 Dec. 16, 2021

Related U.S. Application Data

(60) Provisional application No. 62/809,382, filed on Feb. 22, 2019.

(51) Int. Cl.
*A61K 35/74* (2015.01)
*A61P 35/00* (2006.01)
*C07K 14/255* (2006.01)
*C12N 1/20* (2006.01)
*C12N 9/12* (2006.01)

(52) U.S. Cl.
CPC .............. *A61K 35/74* (2013.01); *A61P 35/00* (2018.01); *C07K 14/255* (2013.01); *C12N 1/20* (2013.01); *C12N 9/1205* (2013.01); *C12Y 207/0104* (2013.01)

(58) Field of Classification Search
None
See application file for complete search history.

(56) References Cited

U.S. PATENT DOCUMENTS

| | | |
|---|---|---|
| 2009/0175829 A1 | 7/2009 | Forbes et al. |
| 2011/0293567 A1 | 12/2011 | Eils et al. |
| 2013/0209405 A1 | 8/2013 | Curtiss, III et al. |
| 2017/0095552 A1 | 4/2017 | Szalay et al. |
| 2017/0224806 A1 | 8/2017 | Curtiss, III et al. |
| 2017/0275340 A1 | 9/2017 | Yun et al. |

FOREIGN PATENT DOCUMENTS

WO    WO-2011150421 A2 * 12/2011 ............. A61K 35/74

OTHER PUBLICATIONS

Supporting Information. Kong et al. 10.1073/pnas.0803801105, 2008.*
Kong et al. "Palmitoylation State Impacts Induction of Innate and Acquired Immunity by the *Salmonella enterica* Serovar Typhimurium msbB Mutant," Infection and Immunity, Dec. 1, 2011 (Dec. 1, 2011), vol. 79, No. 12, pp. 5027-5038.
Nguyen et al. "Genetically Engineered *Salmonella typhimurium* as an Imageable Therapeutic Probe for cancer," Cancer Research, Jan. 1, 2010 (Jan. 1, 2010), vol. 70, No. 1, pp. 18-23.
Shi et al. "Angiogenic Inhibitors Delivered by the Type III Secretion System of Tumor-Targeting *Salmonella typhimurium* Safely Shrink Tumors in Mice," AMB Express, Aug. 24, 2016 (Aug. 24, 2016), vol. 6, pp. 1-10.
Zheng et al. "Targeted Cancer Therapy Using Engineered *Salmonella typhimurium*," Chonnam Med J, Sep. 23, 2016 (Sep. 23, 2016), vol. 52, No. 3, pp. 173-184.

* cited by examiner

*Primary Examiner* — Oluwatosin A Ogunbiyi
(74) *Attorney, Agent, or Firm* — Quarles & Brady LLP

(57) ABSTRACT

The present disclosure relates to genetically modified strains of *Salmonella*, engineered to be tumor navigating and to alter tumor metabolism in the tumor microenvironment. Also provided herein are methods of producing and methods of using such genetically modified *Salmonella* strains to treat cancer.

15 Claims, 9 Drawing Sheets
(5 of 9 Drawing Sheet(s) Filed in Color)
Specification includes a Sequence Listing.

USING TUMOR-NAVIGATING *SALMONELLA* TO MODULATE TUMOR METABOLISM

CROSS-REFERENCE TO RELATED APPLICATIONS

This application is a national stage application filed under 35 U.S.C. § 371 of International Application No. PCT/US2020/019110, filed Feb. 20, 2020, which claims the benefit of U.S. Provisional Application Ser. No. 62/809,382, filed Feb. 22, 2019, both of which are incorporated by reference herein as if set forth in their entirety.

STATEMENT REGARDING FEDERALLY FUNDED RESEARCH OR DEVELOPMENT

Not applicable.

REFERENCE TO THE SEQUENCE LISTING

This application is being filed electronically via EFS-Web and includes an electronically submitted Sequence Listing in .txt format. The .txt file contains a sequence listing entitled "2020-02-20_112624-01158_ST25.txt" created on Jan. 23, 2020 and is 30,245 bytes in size. The Sequence Listing contained in this .txt file is part of the specification and is hereby incorporated by reference herein in its entirety.

BACKGROUND

Despite many advances in conventional methods such as chemo- and radiation-therapy, cancer treatment is still far from optimal. Current cancer therapies frequently encounter challenges including nonspecific systemic distribution of antitumor agents, inadequate drug concentrations reaching the tumor site, intolerable cytotoxicity and development of multiple drug resistance. Oncolytic bacterial therapy has been extensively studied in recent years to fill the critical unmet needs of cancer patients, where the current treatment options have been exhausted. However, the accumulation of genetic mutations and the potential for acquisition of antibiotic-resistance in the therapeutic bacteria present possible risks for recipients of oncolytic bacterial therapy. Accordingly, there remains a need for improvements to existing oncolytic bacteria-based cancer treatments and, in particular, there is a need to develop new therapeutic compositions and methods that employ tumor-navigating, self-eradicating oncolytic *Salmonella* for modulating tumor metabolism within the tumor microenvironment and for targeted delivery of decoy binding partners.

SUMMARY OF THE DISCLOSURE

The present disclosure addresses the aforementioned drawbacks of conventional methods for treating cancer. In a first aspect, provided herein.

In a first aspect, provided herein is a genetically modified *Salmonella* bacterium, wherein the bacterium comprises a first recombinant gene encoding for constitutive glucose transporter EIICB$^{GLC}$ synthesis; a second recombinant gene encoding for increased expression of a methyl-accepting chemotaxis protein (MCP); one or more of mutations ΔpykA, ΔpykE, ΔsseL, ΔspvD, and ΔssrAB, wherein the modified bacterium is capable of self-eradication in non-tumor cells and exhibits increased tumoricidal activity relative to a *Salmonella* bacterium not comprising the first recombinant gene and the one or more of mutations ΔpykA, ΔpykE, ΔsseL, ΔspvD, and ΔssrAB. The genetically modified *Salmonella* bacterium can further comprise a third recombinant gene encoding a decoy polypeptide. The decoy polypeptide can disrupt Wnt/β-catenin signaling. The decoy polypeptide can be a soluble form of human frizzled (FZD) receptor or a soluble form of human LRP6. The bacterium can comprise mutation $\Delta P_{tar}::P_{trc\ \Delta lacO}$ tar. The bacterium can comprise mutations $\Delta P_{tar}::P_{trc\ \Delta lacO}$ tar, $\Delta P_{tsr}::P_{trc\ \Delta lacO}$ tsr, and Δtrg. The bacterium can be a strain set forth in Table 1.

In another aspect, provided herein is a method of treating a tumor in a subject in need thereof comprising administering a genetically modified *Salmonella* bacterium of this disclosure to the subject, whereby the genetically modified *Salmonella* bacterium treats tumor cells in the subject. Administrating can comprise oral administration or intra-tumoral injection of the genetically modified *Salmonella* bacterium.

In another aspect, provided herein is a method for stimulating tumoricidal activity in a host comprising: transforming a first recombinant gene into a regulated attenuation strain of *Salmonella* forming engineered strain B, the first recombinant gene encoding for constitutive glucose transporter EIICB$^{GLC}$ synthesis; transforming a second recombinant gene into engineered strain B forming engineered strain C, the second recombinant gene encoding for chemotaxis of engineered strain B toward a plurality of tumor cells; transforming a third recombinant gene into engineered strain C forming engineered strain D, the third recombinant gene encoding one or more of mutations ΔpykA and ΔpykE; and administering engineered strain D to the host. Engineered strain D can further comprise a fourth recombinant gene encoding a decoy polypeptide that disrupts Wnt/β-catenin signaling. The decoy polypeptide can be a soluble form of human frizzled (FZD) receptor or a soluble form of human LRP6. Administering can comprise oral administration or intra-tumoral injection of engineered strain D into the host. Engineered strain D can be a strain set forth in Table 1. Engineered strain D can further comprise a fourth recombinant gene encoding one or more mutations selected from ΔsseL, ΔspvD, and ΔssrAB, whereby the further engineered strain exhibits enhanced activated T cell activity upon administration in the host. The further engineered strain can be a strain set forth in Table 1.

These and other advantages and features of the present disclosure will become more apparent from the following detailed description of the preferred embodiments of the present disclosure when viewed in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
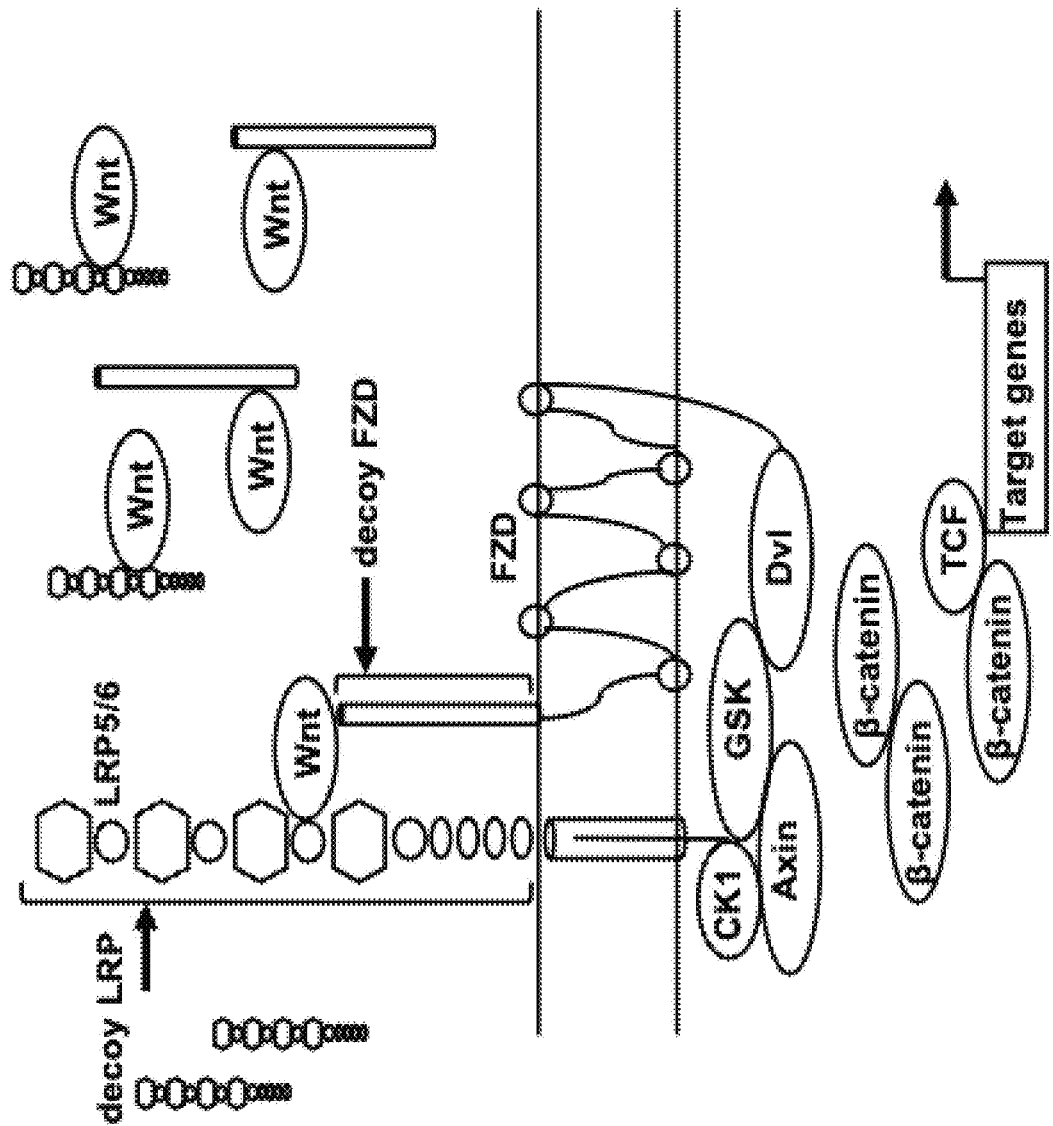
FIG. 1 illustrates the disruption of the Wnt/β-catenin pathway by decoy FZD and decoy LRP5/6.

The present disclosure addresses the aforementioned drawbacks of conventional methods for treating cancer, including current uses of oncolytic bacteria in cancer treatments. In particular, the methods and compositions described herein are based at least in part on the inventor's development of genetically modified *Salmonella* (GMS) capable of precise navigation to tumors and self-eradication. The GMS are further engineered to (i) deprive glucose of a tumor microenvironment in order to reduce cancer cell-mediated lactate production, which will restore tumor infiltrated T-cell activity; and (ii) convert glucose to phosphoenolpyruvate (PEP) and release PEP into the tumor microenvironment (TME) to metabolically reprogram tumor-specific CD4 and CD8 T cells. The present disclosure provides GMS-based compositions and therapeutic strategies for treating cancer based on the ability of tumor-navigating, self-eradicating GMS strains to modulating tumor metabolism within the TME and, in some cases, to additionally deliver decoy peptides that disrupt signal transduction cascades within the TME. Without being bound to any particular mode of action or theory, the GMS-based cancer therapeutic strategies of this disclosure are based on the ability of tumor-navigating, self-eradicating GMS strains having upregulated glucose import to take up glucose regardless the bacterium's intracellular glucose and, thus, deprive the TME of glucose.

Accordingly, in a first aspect, provided herein is a genetically modified *Salmonella* bacterium, where the bacterium comprises a first recombinant gene providing for constitutive glucose transporter EIICB$^{GLc}$ synthesis, a second recombinant gene encoding for increased expression of a methyl-accepting chemotaxis protein (MCP), and a third recombinant gene encoding for reduced toxicity of the bacterium in a plurality of non-tumor cells and for toxicity of the bacterium in tumor cells. As described and demonstrated herein, such genetically modified *Salmonella* bacteria are capable of self-eradication and specific delivery of decoy peptides to tumor cells. Such GMS also exhibit increased tumoricidal activity relative to a *Salmonella* bacterium not comprising the first recombinant gene.

Some embodiments of the instant disclosure comprise a species or subspecies of the *Salmonella* genera. For instance, the recombinant bacterium may be a *Salmonella enterica* serovar. In an exemplary embodiment, a bacterium of the disclosure may be derived from (i.e., an isolate of) *S. enterica* serovar *typhimurium*, referred to herein as *Salmonella typhimurium*, and also from *S. typhi*, *S. paratyphi*, *S. enteritidis*, *S. choleraesius*, *S. arizona*, or *S. dublin*. In an exemplary embodiment, the recombinant bacterium is derived from *S. typhimurium*. As used herein, "*Salmonella typhimurium*" refers to an isolate of *Salmonella typhimurium*. Likewise, the terms "*S. typhi*," "*S. paratyphi*," "*S. enteritidis*," "*S. choleraesius*," "*S. arizona*," and "*S. dublin*" as used herein refer to isolates of *Salmonella typhi*, *S. paratyphi*, *S. enteritidis*, *S. choleraesius*, *S. arizona*, and *S. dublin*, respectively. As used herein the terms "strain" and "isolate" are used interchangeably.

In some cases, the genetic modification comprises replacing the promoter region of glucose transporter geneptsG in *Salmonella* with a P$_{trc\Delta lacO}$ promoter, which is not affected by LacI repressor, for constitutive glucose transporter EIICB$^{GLc}$ synthesis.

In some cases, the genetically modified *Salmonella* bacterium additionally comprises genetic modifications that delete two isoforms of pyruvate kinase, PykA and PykF. *Salmonella* comprising such PykA and PykE deletions (ΔpykA and ΔpykE) convert glucose to PEP instead of lactate and, thus, block lactic acidosis and prevent cancer cells from using lactic acidosis to escape glucose deprivation.

In some cases, the genetically modified bacterium is further modified such that the recombinant bacterium exhibits a reduced expression of immunosuppressive membrane proteins, which are typically overexpressed during *Salmonella* infection. Generally speaking, the bacterium comprises chromosomal gene mutations, largely originates from the *Salmonella* pathogenicity island 2 (SPI2), which encodes proteins associated with induction of programmed death-ligand 1 (PD-L1) expression. PD-L1 is an immunosuppressive membrane protein that binds to T cells via the PD-1 receptor and thereby halts their activation. PD-L1 expression plays an essential role in the immunological tolerance of self-antigens but is also exploited for immune evasion by pathogen-infected cells and cancer cells. It has been demonstrated that *Salmonella* infection of intestinal epithelial cells combined with gamma interferon (IFNγ) causes the synergistic induction of PD-L 1 . The increased expression of PD-L1 through *Salmonella* infection was seen in both human and rat intestinal epithelial cell lines. It was determined that cellular invasion by the bacteria is necessary for PD-L1 induction, potentially indicating that Salmonella strains are delivering mediators from inside the host cell that triggers the increased PD-L1 expression. In addition, Salmonella plus IFNγ induction of PD-L1 decreased the cytokine production of activated T cells.

In some cases, the genetically modified Salmonella bacterium additionally comprises one or more genetic modifications that delete gene sseL, spvD, and/or ssrAB. Salmonella comprising SseL (ΔsseL), SpvD (ΔspvD), and/or SsrAB (ΔssrAB) deletions exhibit decreased expression of an immunosuppressive membrane protein PD-L1, after Salmonella infection and, thus, enhance the activation of host T-cells relative to Salmonella not comprising that additional genetic modifications. The term "sseL" refers to a gene encoding sulfatase/phosphatase/protease, which acts as a deubiquitinase in infected host cells. The term "spvD" refers to a gene encoding cysteine hydrolase, which negatively regulates the NF-κB signaling pathway and promotes virulence of S. typhimurium in mice. The term "ssrAB" refers to chromosomal loci located within SPI-2, which encodes two-component regulatory system SsrAB, which regulates the expression of several operons in SPI-2 and, in addition, a large number of genes for non-SPI2-encoded effector proteins. Knockout mutants, including but not limited to ΔsseL, ΔspvD or ΔssrAB, cause the absence of the function of specific proteins to prevent the induction of PD-L1 expression. In some embodiments, the mutations are combined to maximize the effect of selected mutations.

In certain embodiments, a genetically modified bacterium of the disclosure may also be attenuated. As used herein, the term "attenuated" refers to the state of the bacterium wherein the bacterium has been weakened from its wild-type fitness by some form of recombinant or physical manipulation such that the bacterium's virulence is reduced relative to a control (a non-recombinant/non-manipulated bacterium). This includes altering the genotype of the bacterium to reduce its ability to cause disease. However, the bacterium's ability to colonize the tumor is, preferably, not substantially compromised. For instance, in one embodiment, regulated attenuation allows the recombinant bacterium to express one or more nucleic acids encoding products important for the bacterium to withstand stresses encountered in the host after immunization. This allows efficient invasion and colonization of tumor tissues before the genetically modified bacterium is regulated to display the attenuated phenotype. As used herein in this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the appropriate control.

Any appropriate method can be used to confirm molecular genetic attributes metabolic function of in genetically modified Salmonella bacteria of this disclosure. For example, molecular genetic attributes can be confirmed using polymerase chain reaction (PCR) and sequencing. In some cases, LC-MS/MS assays may be performed to confirm enhanced glucose up-taking and accumulation of glycolytic metabolite PEP in such genetically modified Salmonella bacteria.

As used herein, the terms "genetically modified" and "genetically engineered" are used interchangeably and refer to a prokaryotic cell that includes an exogenous polynucleotide, regardless of the method used for insertion. In some cases, the cell has been modified to comprise a non-naturally occurring nucleic acid molecule that has been created or modified by the hand of man (e.g., using recombinant DNA technology) or is derived from such a molecule (e.g., by transcription, translation, etc.). A cell that contains an exogenous, recombinant, synthetic, and/or otherwise modified polynucleotide is considered to be an engineered cell. The term "altered," as used herein, refers to any change in the nucleic acid sequence that results in the nucleic acid sequence not being expressed. In an exemplary embodiment, the alteration results in the nucleic acid sequence not being expressed in a host. In one embodiment, the alteration is a deletion. In another embodiment, the alteration places an essential nucleic acid under the control of a regulatable promoter, such that the nucleic acid is not expressed in a host.

For genetically modified Salmonella, non-limiting examples of nucleic acid sequences which may be used for attenuation include: a pab nucleic acid sequence, a pur nucleic acid sequence, an aro nucleic acid sequence, asdA, a dap nucleic acid sequence, murA, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hilA, rpoE, flgM, tonB, slyA, and any combination thereof. Generally, the nucleic acids provided above as non-limiting examples encode "attenuation proteins," meaning any protein the absence of which attenuates a bacterium. The "Δ" as used herein, refers to gene deletion. The "::" as used herein, refers to gene insertion. The term "asdA" as used herein, refers to a gene encoding aspartate-semialdehyde dehydrogenase. The asdA mutants of Gram-negative bacteria have an obligate requirement for diaminopimelic acid (DAP), which is an essential constituent of the peptidoglycan layer of the cell wall of these organisms. The "murA" refers to a gene required for the synthesis of the peptidoglycan layer of the bacterial cell wall. Like asdA mutants, murA mutants ("ΔmurA") are deficient in bacterial cell wall synthesis.

In some cases, GMS of this disclosure are engineered for increased chemotaxis toward tumor cells by increasing expression of tar and/or increasing expression or Tsr. In some cases, genetic modification further comprises reducing the expression of Trg. For example, a bacterium can be genetically altered to produce modified Salmonella having constitutive over-expression of one or more chemoreceptors such as Tar and Tsr. In some cases, a genetically modified Salmonella bacterium comprises mutation $\Delta P_{tar}::P_{trc\,\Delta lacO}$ tar. In other cases, the genetically modified Salmonella bacterium comprises mutations $\Delta P_{tar}::P_{trc\,\Delta lacO}$ tar, $\Delta P_{tsr}::P_{trc\,\Delta lacO}$ tsr, and Δtrg.

In some cases, the genetically modified Salmonella bacterium is derived from strain GMS410, GMS515, GMS410 (pK5079), or GMS515(pK5079), which comprise self-eradication vectors, TRAIL, and/or MCP mutations as described herein for increased chemotaxis to tumor cells. For example, strain GMS515 can be modified to replace the promoter region of glucose transporter gene ptsG with a $P_{trc\Delta lacO}$ promoter, which will not be affected by LacI repressor, for constitutive glucose transporter EIICBGLC synthesis. The resulting strain is named GMS516. In some cases, GMS516 is further modified to delete two isoforms of pyruvate kinase, PykA and PykF, producing strain GMS517. The TRAIL-expressing vector pK5079 (or vector control pYA3681) may be transformed into strain GMS517 to produce GMS517(pK5079) (and control GMS517 (pYA3681)).

In some cases, GMS517 is further modified to delete a gene encoding deubiquitinase SseL, thus producing strain GMS530. In some cases, GMS517 is further modified to delete a gene encoding cysteine hydrolase SpvD, thus producing strain GMS531. In other cases, GMS517 is further modified to delete a gene encoding a two-component regulatory system, SsrAB, thus producing strain GMS532. The TRAIL-expressing vector pK5079 (or vector control pYA3681) may be transformed into strains GMS530, GMS531, and GMS532, to produce GMS530(pK5079), GMS531(pK5079), and GMS532(pK5079) (and controls GMS530(pYA3681), GMS531(pYA3681), and GMS532 (pYA3681)).

In some cases, the genetically modified bacterium further comprises a recombinant gene encoding a decoy polypeptide. In such cases, a "sweets-obsessed strain" is further modified for tumor-specific delivery of decoy polypeptides, such as soluble forms of Frizzled (FZD) or LPR6 receptors. The lysis of the genetically modified *Salmonella* of this disclosure releases GMS-expressed decoy polypeptides, thereby disrupting one or more molecular interactions in targeted signaling cascades within the tumor microenvironment. As used herein, the term "decoy polypeptide" refers to a polypeptide or fragment thereof that is capable of trapping the ligands of the target molecules (e.g., a cell surface receptor) and thus preventing its activation. Preferably, decoy polypeptides are soluble forms of a target protein. In some cases, a decoy polypeptide is a truncated form of the target protein from which the transmembrane domain has been removed by chemical, proteolytic, or recombinant methods.

In some cases, the decoy polypeptide is a polypeptide or fragment thereof that disrupts the Wnt/β-catenin pathway and, consequently, reduces or stops Wnt-regulated gene expression. Contemplated within the scope of embodiments presented herein are variants of Wnt-binding receptor polypeptides that act as decoys for canonical Wnt ligands and block Wnt/β-catenin-mediated signaling. In some cases, the decoy polypeptide comprises all or a portion of the extracellular, Wnt-binding domain of a FZD receptor. For example, as illustrated in FIG. 1, the decoy polypeptide may comprise a human FZD polypeptide, where the polypeptide comprises at least one amino acid modification to increase affinity of the decoy FZD polypeptide binding to a canonical Wnt ligand as compared to the affinity for Wnts of the corresponding wildtype FZD receptor.

In some cases, the decoy polypeptide comprises all or a portion of the extracellular Wnt binding domain of LRP6. For example, as illustrated in FIG. 1, the decoy polypeptide may comprise a human LRP6 polypeptide, where the polypeptide comprises at least one amino acid modification to increase affinity of the decoy LRP6 polypeptide binding to a canonical Wnt ligand as compared to the affinity for Wnts of the corresponding wildtype LRP6 receptor.

To produce decoy polypeptides, DNA sequences of Wnt binding domains of human FZD (UniProtKB-Q9UP38) and LRP6 (GenBank: AF074264.1) may be codon-optimized and synthesized in vitro. In some cases, the codon-optimized human FZD and LRP6 DNA fragments can be inserted into a lysis vector (e.g., pYA3681) and then transformed into a tumor-navigating strain (e.g., GMS515, GMS517, GMS530, GMS531, and GMS532). In some cases, the resulting strains are those set forth in Table 1. In some cases, a single decoy polypeptide-expressing strains can be used. In other cases, two or more decoy polypeptide-expressing strains can be used together as a combined therapeutic. See, for example, Table 1.

TABLE 1

GMS strains for solo and combined therapeutics

| Group | | Description |
|---|---|---|
| 1 | PBS | Tumor-bearing mice |
| 2 | GM5517 (pYA3681) | Sweets-obsessed strain harbors empty lysis vector |
| 3 | GM5515 (pK5079) | tumor-navigating GMS expressing TRAIL |
| 4 | GM5517 (pK5079) | Sweets-obsessed GMS expressing TRAIL |
| 5 | GMS517 (pK-FZD) | Sweets-obsessed GMS strain expressing decoy FZD |
| 6 | GM5517 (pK-LRP6) | Sweets-obsessed GMS expressing decoy LRP6 |
| 7 | GM5517 (pK-FZD) and GM5517 (pK-LRP6) | Sweets-obsessed GMS expressing FZD and LRP6 |
| 8 | GM5517 (pK5079), GM5517 (pK-FZD), and GM5517 (pK-LRP6) | Sweets-obsessed GMS expressing TRAIL, FZD, and LRP6 |
| 9 | GM5530 (pYA3681) | Sweets-obsessed GMS strain with ΔsseL mutation harbors empty lysis vector |
| 10 | GM5530 (pK5079) | Sweets-obsessed GMS strain with ΔsseL mutation expressing TRAIL |
| 11 | GMS530 pK-FZD) | Sweets-obsessed GMS strain with ΔsseL mutation expressing decoy FZD |
| 12 | GM5530 (pK-LRP6) | Sweets-obsessed GMS with ΔsseL mutation expressing decoy LRP6 |
| 13 | GM5530 (pK-FZD) and GM5530 (pK-LRP6) | Sweets-obsessed GMS with ΔsseL mutation expressing FZD and LRP6 |
| 14 | GM5530 (pK5079), GM5530 (pK-FZD), and GM5530 (pK-LRP6) | Sweets-obsessed GMS with ΔsseL mutation expressing TRAIL, FZD, and LRP6 |
| 15 | GM5531 (pYA3681) | Sweets-obsessed GMS strain with ΔspvD mutation harbors empty lysis vector |
| 16 | GM5531 (pK5079) | Sweets-obsessed GMS strain with ΔspvD mutation expressing TRAIL |
| 17 | GM5531 (pK-FZD) | Sweets-obsessed GMS strain with ΔspvD mutation expressing decoy FZD |
| 18 | GM5531 (pK-LRP6) | Sweets-obsessed GMS strain with ΔspvD mutation expressing decoy LRP6 |
| 19 | GM5531 (pK-FZD) and GM5531 (pK-LRP6) | Sweets-obsessed GMS strain with ΔspvD mutation expressing FZD and LRP6 |
| 20 | GM5531 (pK5079), GM5531 (pK-FZD), and GM5531 (pK-LRP6) | Sweets-obsessed GMS strain with ΔspvD mutation expressing TRAIL, FZD, and LRP6 |
| 21 | GMS532 (pYA3681) | Sweets-obsessed GMS strain with ΔssrAB mutation harbors empty lysis vector |
| 22 | GM5532 (pK5079) | Sweets-obsessed GMS strain with ΔssrAB mutation expressing TRAIL |
| 23 | GM5532 (pK-FZD) | Sweets-obsessed GMS strain with ΔssrAB mutation expressing decoy FZD |
| 24 | GM5532 (pK-LRP6) | Sweets-obsessed GMS strain with ΔssrAB mutation expressing decoy LRP6 |
| 25 | GM5532 (pK-FZD) and GM5532 (pKLRP6) | Sweets-obsessed GMS strain with ΔssrAB mutation expressing FZD and LRP6 |
| 26 | GM5532 (pK5079), GM5532 (pK-FZD), and GM5532 (pK-LRP6) | Sweets-obsessed GMS strain with ΔssrAB mutation expressing TRAIL, FZD, and LRP6 |

To construct suicide vectors for creating GMS strains GMS516 and GMS517, suicide vectors pK4960 ($AP_{ptsG}$::$P_{trc\ \Delta lacO}$ ptsG), pK4961 ΔpykA), and pK4962 (ΔPykF) were constructed using primers listed in Table 2. Briefly, DNA cassettes (the upstream DNA flanking sequence-downstream flanking sequence) were inserted into the suicide vector pRE112 (Table 1). Suicide vectors pK4960 ($\Delta P_{ptsG}$::$P_{trc\ \Delta lacO}$ ptsG), pK4961 (ΔpykA), and pK4962 (ΔPykF) were constructed by inserting the upstream DNA flanking sequence-promoter $P_{trc\Delta LacO}$—ptsG gene sequence (for pK4960), the upstream DNA flanking sequence—downstream flanking sequence of pykA gene for pK4961, and the upstream DNA flanking sequence—downstream flanking sequence of pykF gene for pK4962 into suicide vector pRE112, respectively. To test the effect of these mutations, each single mutation will be created in *Salmonella* by conjugating wild-type strain χ3761 with *E. coli* strain χ7213 carrying suicide vector pK4960, pK4961, or pK4962. Then, single mutation ($\Delta P_{ptsG}$::$P_{trc\ \Delta lacO}$ ptsG), pK4961 (ΔpykA), and pK4962 (APykF) will be introduced into strain GMS515 by conjugation, respectively.

Nucleic acid sequences for plasmids pK4960, pK4961, and pK4962 are provided as SEQ ID NO:2, SEQ ID NO:3, and SEQ ID NO:4, respectively.

In another aspect, provided herein are methods for producing genetically modified *Salmonella* bacteria having increased tumoricidal activity. In exemplary embodiments, the method comprises: transforming a first recombinant gene into a regulated attenuation strain of *Salmonella* forming a strain B, the first recombinant gene encoding for constitutive glucose transporter EIICB$^{GLC}$ synthesis; transforming a second recombinant gene into the strain B forming a strain C, the second recombinant gene encoding for chemotaxis of the strain B toward a plurality of tumor cells; transforming a third recombinant gene into the strain C forming a strain D, the third recombinant gene encoding one or more of mutations ilpykA and ilpykE; and administering strain D to the host. Strain D can further comprise a fourth recombinant gene encoding a decoy polypeptide that disrupts Wnt/β-catenin signaling. The decoy polypeptide can be a soluble form of human FZD receptor or a soluble form of human LRP6. Administering can comprise oral administration or intra-tumoral injection of strain D into the host. Strain D can be a strain set forth in Table 1.

In another aspect, provided herein is a method for enhancing activated T cell activity in a host. In exemplary embodi-

TABLE 2

Primers for Construction of Suicide Vectors

| Name | Sequence |
|---|---|
| pK4960 | |
| pstG Primer 1 | 5' CCAAGCTTCGCGGTAAAGAGAACCAGCCTGCG (SEQ ID NO: 5) |
| pstG Primer 2 | 5' TGGTTCGTCGTAACAGGTGCCTACGCATCTACACATTATACGAGCCGGAT GATTAATTGTCAACAGCTCATTTCAGAATAATTGAGAGTGCTCCT (SEQ ID NO: 6) |
| pstG Primer 3 | 5' CTGTTACGACGAACCACACAGGAAACAGACCATGTTTAAGAATGCATTTG CTAACCTGCAAAAGGTCGGTAAATCGCTGATGCTGCCGGTATCCGTACTCCC TATCGCAGGTATCCTGC (SEQ ID NO: 7) |
| pstG Primer 4 | 5' GGGAATTCTGCCCGCAAAGAAGCCCAGATACT (SEQ ID NO: 8) |
| pK4961 | |
| pykA Primer 1 | 5' CCAAGCTTATTTCGCATACTGGCAGAACCAAG (SEQ ID NO: 9) |
| pykA Primer 2 | 5' GTAATACTCCGTTGACTAAAACAA (SEQ ID NO: 10) |
| pykA Primer 3 | 5' AACTCCCCCACGCCTGTTCATCAG (SEQ ID NO: 11) |
| pykA Primer 4 | 5' GGGAATTCCGTCAGGGCTACTGGGGTTACTAC (SEQ ID NO: 12) |
| pK4962 | |
| pykF Primer 1 | 5' CCAAGCTTCAACCAAAACATCGCCATCGACCT (SEQ ID NO: 13) |
| pykF Primer 2 | 5' GACAGTCTTAGTCTTTAAGTTGAG (SEQ ID NO: 14) |
| pykF Primer 3 | 5' TAATTGTTGTGTGAATTAATTTGT (SEQ ID NO: 15) |
| pykF Primer 4 | 5' GGGAATTCTCGTTGCTCAGCTGGTCAACTTTA (SEQ ID NO: 16) |

In addition to the introduction of recombinant genes encoding decoy polypeptides as described above, *Salmonella* are also genetically modified to increase navigation of the bacteria to cancer cells (tumor cells) by modulating expression of methyl-accepting chemotaxis proteins (MCP), which are transmembrane chemoreceptors important for taxis (bacterial movement) toward or away from particular substrates. *Salmonella* MCPs include Tar (taxis towards aspartate and maltose, away from nickel and cobalt; aka CheM), Tsr (taxis towards serine, away from leucine, indole and weak acids), Trg (taxis towards sugars, galactose and ribose), Tap (taxis towards dipeptides), McpC (repellent response towards L-cystine), Tip, McpA, and McpB. The coding sequence of Tsr (Methyl-accepting chemotaxis protein) of *Salmonella typhimurium* is accession number A0A0H3NL96. The coding sequence of Tar (Methyl-accepting chemotaxis protein II) of *Salmonella typhimurium* is accession number P02941.

ments, the method comprises transforming a fifth recombinant gene into strain D as described herein, thus forming strain E. In such cases, the fifth recombinant gene encodes one or more genetic modifications that delete gene sseL, ΔspvD, and/or ΔssrAB, such that the resulting recombinant *Salmonella* strain (e.g, Strain E, F, and G, respectively) comprises a SseL deletion (ΔsseL), a SpvD deletion (ΔspvD), and/or a SsrAB deletion (ΔssrAB) and exhibits decreased expression of a deubiquitinase, a cysteine hydrolase, and/or two-component regulatory system SsrAB, respectively. The method further comprises administering the resulting recombinant *Salmonella* strain to a host organism. Administering can comprise oral administration or intra-tumoral injection. In some cases, the resulting recombinant *Salmonella* strain further comprises a recombinant gene encoding a decoy polypeptide (described above) that disrupts Wnt/-catenin signaling. The decoy polypeptide can be a soluble form of human FZD receptor or a soluble form of human LRP6. Administering can comprise oral administration or intra-tumoral injection of Strains E, F, and G into the host. Strain E, F and G can be strain sets ninth, fifteenth, and twenty-first in Table 1, respectively.

The genetically modified *Salmonella* described herein can be used in a variety of applications. For example, the genetically modified *Salmonella* can be used in therapeutic methods to treat cancer or a cancer-associated condition. In some cases, a method of treating cancer in a subject in need thereof will comprise administering an effective amount of a modified *Salmonella* bacterium having the genetic modifications described herein and, thus, being tumor navigating, self-eradicating, and armed with one or more decoy polypeptides, to the subject, whereby the genetically modified *Salmonella* bacterium treats cancer in the subject. As used herein, the term "effective amount" means, in the context of a composition, an amount of an immunogenic composition capable of inducing an immune response that reduces the incidence of or lessens the severity of infection or incident of disease in an animal. Alternatively, in the context of a therapy, the term "effective amount" refers to the amount of a therapy which is sufficient to reduce or ameliorate the severity or duration of a disease or disorder (e.g., cancer), or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent. The effective amount to be administered will depend upon the host receiving the modified bacteria as well as factors such as the size, weight, and age of the host.

As used herein, "subject" refers to an animal or a patient for whom the described treatment is intended. In exemplary embodiments, subjects treated according to the methods provided herein are human. In other cases, subjects treated according to the methods provided herein are non-human mammals, including by way of example and not limitation, members of rodentia (e.g., mouse, rat, guinea pig), lagomorpha (e.g., rabbits, hares), perissodactyla (e.g., horses, donkeys, etc.), artodactyla (e.g., pigs, cows, sheep), carnivora (e.g., cats, canines), and primates (e.g., apes, monkeys, baboons, and humans).

As used herein, the terms "treat" and "treating" refer to both therapeutic treatment and prophylactic or preventative measures, wherein the object is to treat, rescue, ameliorate, or otherwise lessen an undesired symptom or condition associated with cancer or any condition associated with aberrant cell proliferation. In some cases, the term "treated" refers to any beneficial effect on the progression of a disease or condition. Beneficial effects can include reversing, alleviating, inhibiting the progress of, preventing, or reducing the likelihood of the disease or condition to which the term applies or one or more symptoms or manifestations of such a disease or condition. Where the disease or condition is cancer or a cancer-associated condition, treating can refer to the management and care of a patient for the purpose of combating cancer, and can include reversing, alleviating, inhibiting the progress of, preventing, or reducing the likelihood of, or lessening the severity of any aspect of the cancer or cancer-associated condition (e.g., metastasis, tumor growth). As used herein, the terms "preventing" and "prevent" refer not only to a complete prevention of a certain disease or condition, but also to partially or substantially attenuating, reducing the risk of, or delaying the development or recurrence of the disease or condition to which the term applies.

In some cases, the methods provided herein are directed to treating or preventing cancer in a subject by administering a composition provided herein. In other cases, the present disclosure provides a method of inhibiting, retarding, or preventing the growth of a tumor or tumor cells in a subject. In exemplary embodiments, colon cancer (colorectal cancer) is treated using the methods provided herein. Examples of other cancers appropriate for methods of treating or preventing as provided herein include, without limitation, lung cancer, pancreatic cancer, prostate cancer, skin cancer, bladder cancer, kidney cancer, ovarian cancer, colorectal cancer, breast cancer, cervical cancer, brain cancer, esophageal cancer, and stomach cancer. Other diseases or conditions appropriate for methods of treating or preventing as provided herein include, without limitation, lymphoma and chronic and acute leukemia.

Any appropriate route or mode of administration to the subject can be employed according to a method provided herein. In some cases, administering comprises oral administration of the genetically modified *Salmonella* bacterium. In other cases, administering comprises intra-tumoral injection of the genetically modified *Salmonella* bacterium. The mode of administration can be determined based on the physical location, type, or number of tumors in the subject's body.

Clinicians, physicians, and other health care professionals can administer genetically modified *Salmonella* bacteria to a subject in need thereof according to a method provided herein. In some cases, a single administration of the composition may be sufficient. In other cases, more than one administration of the composition is performed at various intervals (e.g., once per week, twice per week, daily, monthly) or according to any other appropriate treatment regimen. The duration of treatment can be a single dose or periodic multiple doses for as long as the administration of a composition provided herein is tolerated by the subject.

Any appropriate method can be practiced to determine, detect, or monitor a subject's response to treatment according to a method provided herein. As used herein, "determining a subject's response to treatment" refers to the assessment of the results of therapy in a subject in response to administration of a composition provided herein or to treatment according to a method provided herein. For example, a subject's condition can be monitored continuously or evaluated at appropriate time intervals (e.g., at regular or irregular time points) to detect and/or monitor any changes in disease progression (e.g., change in tumor size) as an indicator of the subject's response to a composition comprising genetically modified *Salmonella* bacteria as described herein. In some cases, tumors can be measured to detect or monitor any change in, for example, tumor size or tumor growth rate (e.g., tumor expansion or shrinkage, inhibited or accelerated tumor growth rate). For example, detection methods such as computed tomography (CT), magnetic resonance imaging (MRI) scanning, and x-ray (e.g., chest x-ray) can be used. In some cases, ultrasound examinations can be used to detect and measure tumor regression or to detect the progression of lesions. In other cases, evaluation of a tumor can involve cytology or histology of, for example, biopsy samples. For solid tumors, evaluation of a subject's response to treatment as provided herein can include assessing RECIST ("Response Evaluation Criteria in Solid Tumors"). RECIST criteria can be used to evaluate a subject's response to the therapy used to treat their disease or condition. See, for review, Therasse et al., *J. Natl. Cancer Inst.* 92:205-16, 2000.

The term "promoter", as used herein, may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of the same.

The terms "nucleic acid" and "nucleic acid molecule," as used herein, refer to a compound comprising a nucleobase and an acidic moiety, e.g., a nucleoside, a nucleotide, or a polymer of nucleotides. Nucleic acids generally refer to polymers comprising nucleotides or nucleotide analogs joined together through backbone linkages such as but not limited to phosphodiester bonds. Nucleic acids include deoxyribonucleic acids (DNA) and ribonucleic acids (RNA) such as messenger RNA (mRNA), transfer RNA (tRNA), etc. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, small interfering RNA (siRNA), small nuclear RNA (snRNA), a plasmid, cosmid, chromosome, chromatid, or other naturally occurring nucleic acid molecules. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or include non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadeno sine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acids and/or other constructs of the disclosure may be isolated. As used herein, "isolated" means to separate from at least some of the components with which it is usually associated whether it is derived from a naturally occurring source or made synthetically, in whole or in part.

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain.

Nucleic acids, proteins, and/or other moieties of the disclosure may be purified. As used herein, purified means separate from the majority of other compounds or entities. A compound or moiety may be partially purified or substantially purified. Purity may be denoted by weight measure and may be determined using a variety of analytical techniques such as but not limited to mass spectrometry, HPLC, etc.

In interpreting this disclosure, all terms should be interpreted in the broadest possible manner consistent with the context. It is understood that certain adaptations of the disclosure described in this disclosure are a matter of routine optimization for those skilled in the art, and can be implemented without departing from the spirit of the disclosure, or the scope of the appended claims.

So that the compositions and methods provided herein may more readily be understood, certain terms are defined:

As used in this specification and the appended claims, the singular forms "a," "an," and "the" include plural references unless the context clearly dictates otherwise. Any reference to "or" herein is intended to encompass "and/or" unless otherwise stated.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Embodiments referenced as "comprising" certain elements are also contemplated as "consisting essentially of" and "consisting of" those elements. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having the same name (but for the use of the ordinal term), to distinguish the claim elements.

The terms "about" and "approximately" shall generally mean an acceptable degree of error for the quantity measured given the nature or precision of the measurements. Typical, exemplary degrees of error are within 10%, and preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Unless otherwise defined, all technical terms used herein have the same meaning as commonly understood by one of ordinary skill in the art to which this disclosure belongs. As used herein and in the claims, the singular forms "a," "an," and "the" include the singular and the plural reference unless the context clearly indicates otherwise. Thus, for example, a reference to "an agent" includes a single agent and a plurality of such agents. Any reference to "or" herein is intended to encompass "and/or" unless otherwise stated.

Various exemplary embodiments of compositions and methods according to this disclosure in addition to those shown and described herein will become apparent to those skilled in the art from the foregoing description and the following examples and fall within the scope of the appended claims. Those skilled in the art will recognize, or be able to ascertain using no more than routine experimentation, many equivalents to the specific embodiments of the disclosure described herein. Such equivalents are intended to be encompassed by the following claims.

EXAMPLES

The following examples will enable one of skill in the art to more readily understand the principles thereof. The following examples are presented by way of illustration and are not meant to be limiting in any way.

The inventor previously developed a self-destructing *Salmonella* lysis system in which the bacteria are attenuated, yet capable of synthesizing a selected protein or harboring a DNA vaccine, to serve as vaccine delivery platforms against various infectious diseases. The *Salmonella* lysis system contained two components: a lysis *Salmonella* strain and a lysis vector. The *Salmonella* lysis strains harbor a deletion of asdA and the arabinose-regulated expression of mur A, two genes required for the synthesis of the peptidoglycan layer of the bacterial cell wall. They also contain additional mutations intended to enhance bacterial cell lysis and antigen or DNA vaccine delivery. The lysis vector cooperatively works with its host *Salmonella* lysis strain to facilitate the arabinose-dependent bacterial cell wall synthesis needed for bacterial reproduction. Upon invasion of host tissues, which is an arabinose-free environment, synthesis of the bacterial cell wall eventually ceases. This leads to bacterial cell lysis to release cell contents after bacteria accumulate in host tissues and accomplish *Salmonella* self-eradicating. Experiments were undertaken to genetically engineer the lysis strains into a versatile set of tumor navigating anti-cancer material delivering vehicles.

Five to six percent of individuals will develop colorectal cancer (CRC) over their lifetime in the United States. The heavy burden that CRC imposes on our society emphasizes the need to develop effective strategies to prevent and treat this disease. It has been reported that mutations of the adenomatous polyposis coli (APC) gene predispose individuals to familial adenomatous polyposis (FAP), characterized by multiple tumors in the large intestine. Mice carrying a CDX2P -NLS-Cre recombinase transgene and a loxP-targeted Apc allele develop mainly colorectal tumors after tamoxifen induction. A transgenic $Apc^{flox/flox}$/CDX2-CRE colon tumor mouse models greatly mimic human FAP-associated colorectal cancer and sporadic colorectal cancer. Moreover, direct orthotopic cell microinjection, between the mucosa and the muscularis externa layers of the cecal wall of immunocompromised NOD. Cg-Prkdcscid Il2rgtm1Wj1/SzJ (NSG™) mice, induces tumor foci in the most relevant metastatic sites observed in humans. The application of this procedure to the human colorectal cancer cell lines HCT-116 yielded high tumor takes and dissemination rates, replicating the metastatic spread to lymph nodes, liver, lung, and peritoneum observed in advanced human colorectal cancer. To faithfully recapitulate human CRC, in addition to allograft and xenograft subcutaneous tumor models, the transgenic and orthotopic colon tumor mouse models were used to evaluate our re-engineered GMS therapeutic strains on inhibition of tumor growth and cancer metastasis.

The *Salmonella* chemotaxis system was engineered to develop tumor navigating, self-eradicating, and TRAIL-armed genetically engineered *Salmonella*. These GMS hold tumor-navigating features and are able to release TRAIL into tumor bed via *Salmonella* cell lysis leading to the induction of tumor cell apoptosis. These GMS were comprehensively evaluated to assure the safety and demonstrate their efficacy on the suppression of cancer growth and metastasis in subcutaneous, orthotopic, and transgenic colon cancer mouse models. These GMS dramatically induced a variety of types of cancer cell death in vitro. Intra-tumor (IT) injected GMS significantly reduced tumor growth in both allograft and xenograft subcutaneous colon cancer mouse models. Moreover, oral administrated (OR), a convenient and less toxic route than parenteral administration, GMS reduced significant tumor growth in the transgenic CRC mouse model. It inhibited metastasis in the xenograft orthotopic colon cancer mouse model.

Results

Reprogramming *Salmonella* Chemotaxis System for Tumor-Navigating

We have improved our self-eradicating *Salmonella* strains to better serve the delivery purpose. Lysis strain GMS409 was engineered to not only harbor the genetic attributes for self-eradicating feature, but also to display genetic characteristics for regulated delayed attenuation, delayed antigen synthesis, and reduced endotoxic activity. However, such GMS strain could not target either cancer cells or tumors. To transform a vaccine delivery strain GMS409 into a universal tumor-navigating delivery vehicle for cancer therapy, our approach was to reprogram the *Salmonella* chemotaxis system to enhance its chemotaxis toward particular tumor secreting amino acids. Such a strategy will allow maximized GMS tumor-eradicating and release of an anti-cancer agent inside of the tumor during the self-eradicating process to trigger bacteria-based oncolysis.

In order to achieve this goal, we first replaced the promoters of the genes encoding chemoreceptors Tar (tar) and Tsr (tsr), respectively, with the $P_{trc}$ promoter for constitutive chemoreceptor synthesis. *Salmonella* strains GMS371 carrying single deletion-insertion mutation $\Delta P_{tar}::P_{trc\ \Delta lacO}$ tar and GMS372 harboring single deletion-insertion mutation $\Delta P_{tsr:Ptrc\ \Delta lacO}$ tsr were created using *Salmonella* wild-type strain χ3761. The constitutive overexpression of chemoreceptors Tar and Tsr in GMS371 and GMS372, respectively, was confirmed by SDS electrophoresis and western blot assay. In addition, strains GMS371 and GMS372 showed similar growth and swimming speed comparing to their wildtype *Salmonella* parent strain χ3761. Chemotaxis assay was performed to demonstrate the ideal enhancement of chemotaxis caused by each deletion-insertion mutation. We found that GMS371 and GMS372 are significantly more attracted to aspartate and serine, respectively, than the wild-type strain χ3761. To further enhance the *Salmonella* accumulation in the layer of tumor quiescent cells, other than the necrotic core, the ribose/galactose receptor trg gene was deleted. The strain with Δtrg deletion is much less attracted to galactose than wild-type strain as desired. To finally create tumor-navigating, self-eradicating GMS strains, which hopefully will be able to efficiently navigate tumor and release cancer-killing material in the tumor bed, the single mutation $\Delta P_{tar}::P_{trc\ \Delta lacO}$ tar or triple mutations $\Delta P_{tar}::P_{trc\Delta lacO}$ tar, $\Delta P_{tsr}::P_{trc\ \Delta lacO}$ tsr, and Δtrg were introduced into GMS409 to achieve strains GMS410 and GMS515.

Building up Tumor-Targeting Self-Eradicating TRAIL Delivery Vehicles

A human TRAIL-expressing lysis vector pK5079 was constructed by inserting the TRAIL coding sequence into lysis vector pYA3681 to assemble a self-eradicating *Salmonella* lysis system for cancer therapy. The repressor LacI, expressed from the built-in chromosomal lacI gene under arabinose-regulated araC $P_{BAD}$ promoter, will turn off TRAIL synthesis in vitro to avoid the reduced growth rates and a compromised ability to colonization caused by high-level production of foreign protein. Then the tumor-navigating strains GMS410 and GMS515 were armed with TRAIL by carrying plasmid pK5079 for enhanced cancer cell-killing. The strain GMS409(pK5079) was built, without tumor-navigating feature, to serve as a negative control. The expression of TRAIL by pK5079 in GMS strains was confirmed through western blotting analysis.

Figures 2A, 2B:
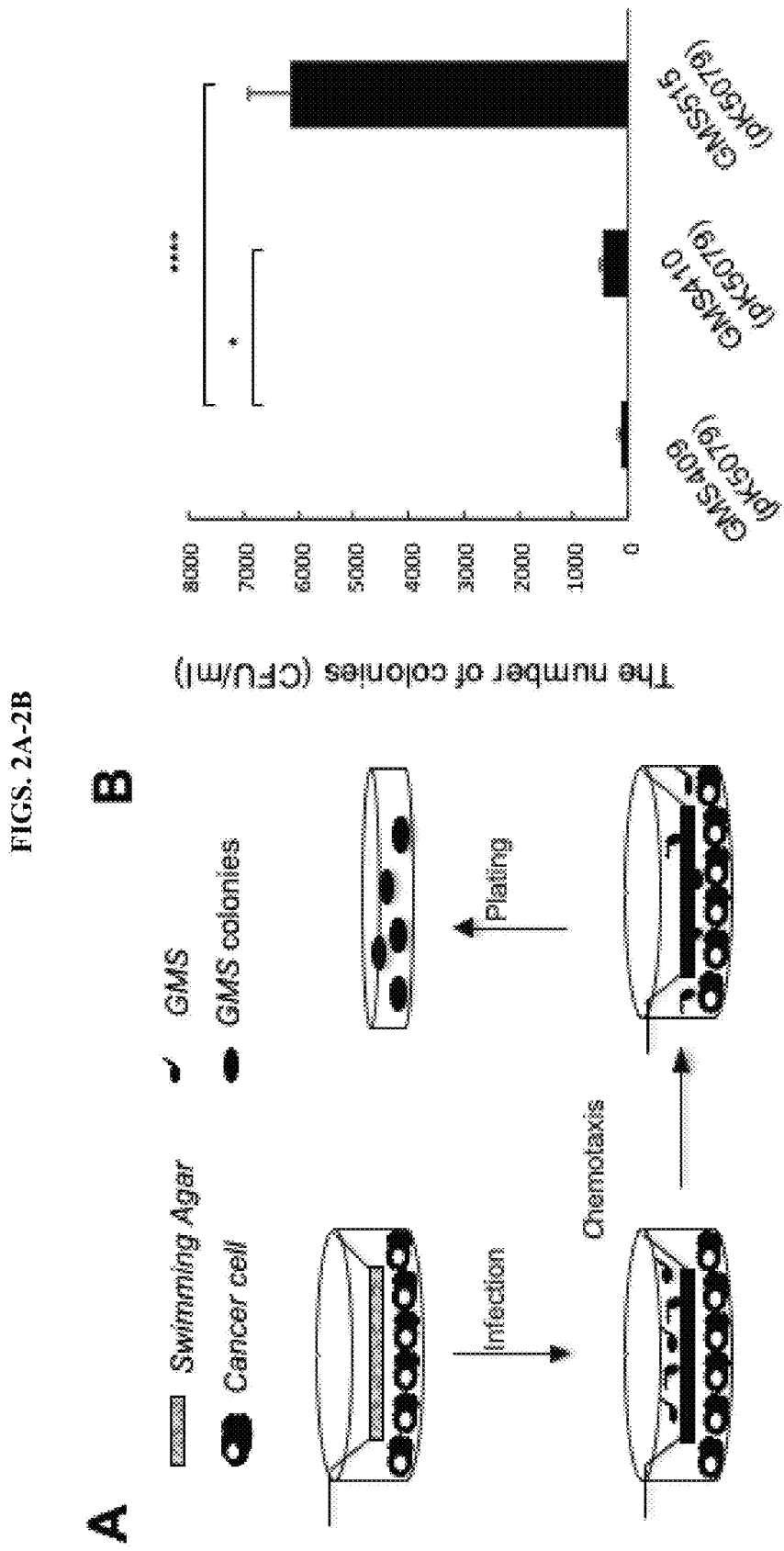
FIGS. 2A-2B demonstrate that reprogramming chemotaxis system of self-eradicating TRAIL-delivering GMS strain facilitates their cancer cell-navigating feature. A. Illustration of transwell assay to determine the colony-forming units (CFU) of GMS swimming cross the swimming agar toward cancer cells. B. The CFU of GMS swimming cross the swimming agar toward human colon cancer cell HCT-116 (*$p<0.05$; $p<0.0001$).
Figure 3:
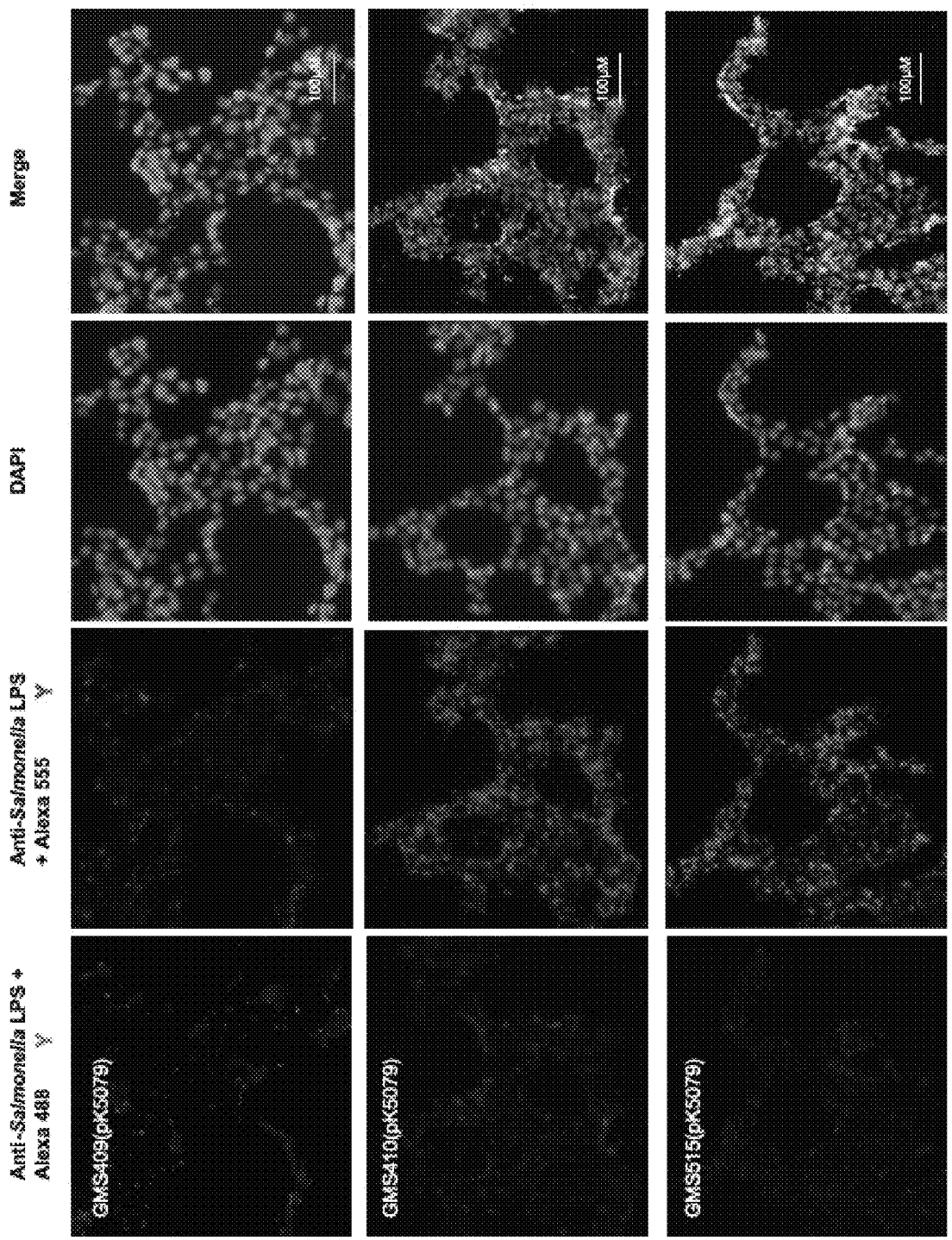
FIG. 3 shows immunofluorescence staining to determine the GMS ability to attach and invade cancer cells. Green, red, and blue fluorescence indicate HCT-116 cell surface attached *Salmonella*, internalized *Salmonella*, and HCT-116 nuclei, respectively.

Reprogrammed Chemotaxis System Endues GMS Strains Superior Ability of Cancer Cell Seeking, Attaching and Invading To validate whether the GMS with chemoreceptor modifications could obtain cancer cell-navigating feature, a transwell culture system was used. A swimming agar layer was used as a barrier between GMS strains and colon cancer cells. GMS strains were cultured in the upper compartment of the transwell culture system, while mouse colon cancer CT-26 or human colon cancer HCT-116 cells were grown in the lower compartment. The swimming agar layer and micropores in the insert membrane allow GMS strains to cross freely (FIG. 2A). It was observed that significantly higher numbers of GMS410(pK5079) and GMS515 (pK5079) swam across the swimming agar layer toward HCT-116 cells, whereas very little numbers of GMS409 (pK5079) did, indicating that reprogrammed chemotaxis system in GMS410(pK5079) and GMS515(pK5079) endue them the cancer cell-navigating ability to seek cancer cells (FIG. 2B). The capability of GMS strains attaching to and invading cancer cells was also examined. The GMS strains were incubated with HCT-116 cells. We found that more GMS410(pK5079) and GMS515(pK5079) attached to and invaded into HCT-116 cells (FIG. 3) comparing to the control strain GMS409(pK5079). These data suggest that chemotaxis system reprogramming in GMS410(pK5079) and GMS515(pK5079) strains to enable them to be better attracted to cancer cells leading to efficient attachment and invasion compared with their parent strain GMS409 (pK5079) without genetically engineered chemotaxis system. Overall, the GMS strains with reprogrammed chemotaxis systems possess superior ability to navigate, attach, and invade colon cancer cells.

Reprogrammed GMS Strains Efficiently Induced Colon Cancer Cell Death In Vitro

Figures 4A, 4B:
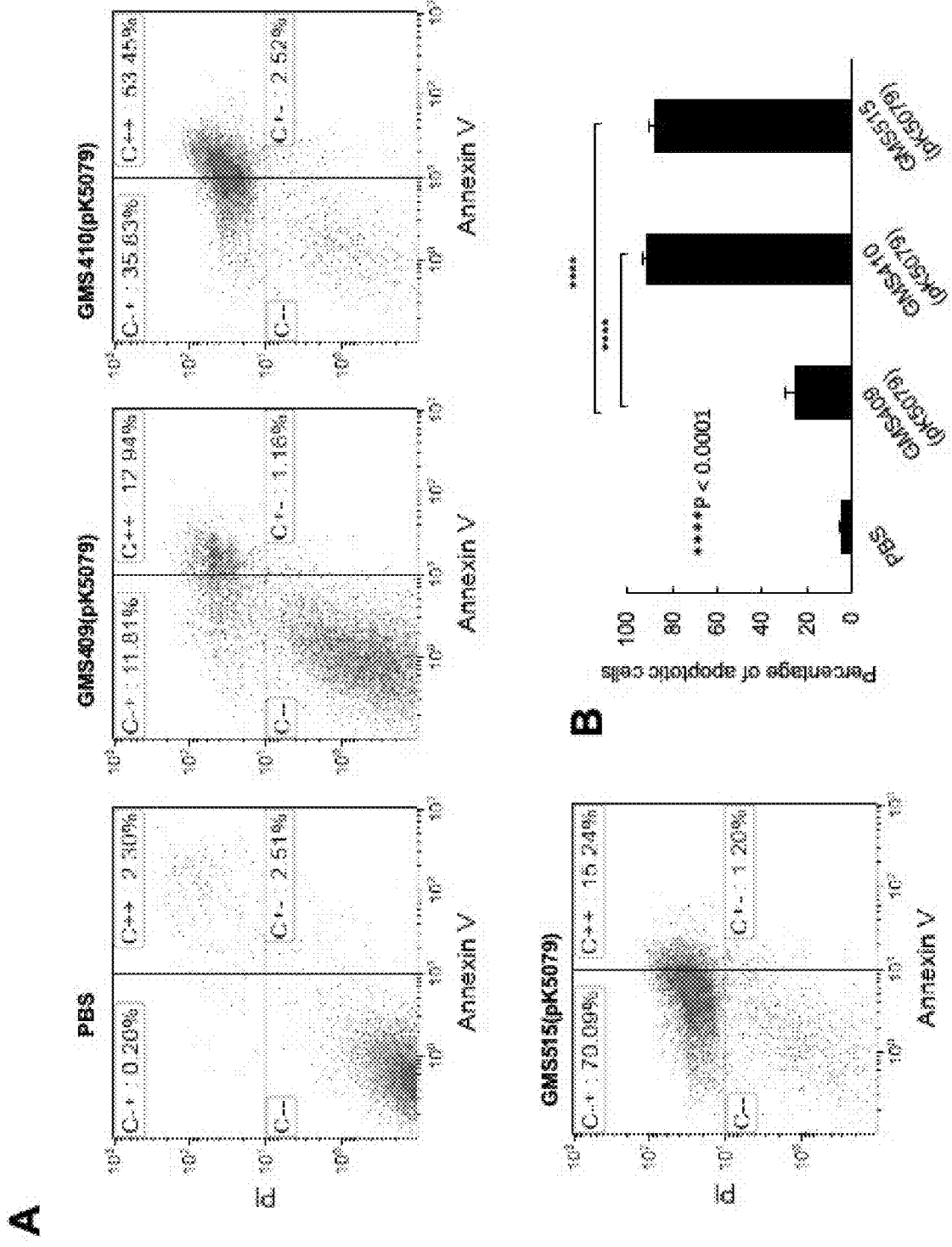
FIGS. 4A-4B demonstrate that reprogrammed GMS strains efficiently induced colon cancer cell death in vitro. A. Representative patterns of apoptosis assays following HCT-116 cells treated with GMS for 16 hours. B. Percentage of apoptotic cells post-treatment. Annexin V-FITC positive HCT-116 cells were expressed as means.

To examine whether the reprogrammed GMS strains have the potential for cancer treatment, the multiple cytotoxic features against cancer cells built into the reprogrammed GMS strains were evaluated in vitro. We first validated the level of activated caspase-3, which is the key "executioner" caspase in the apoptotic cascade, after incubating HCT-116 cells with GMS strains, respectively. It was observed that both cancer cells co-incubated with GMS410(pK5079) or GMS515(pK5079) had higher levels of active caspase-3 protein and lower levels of pro-caspase-3, comparing to the cells co-incubated with GMS409(pK5079). Our results indicate that the self-eradicating TRAIL delivering GMS strains, with reprogrammed chemotaxis system, are able to promote the apoptotic cascade through caspase-3 activation. To further validate the cancer cell-killing features in reprogrammed GMS strains, the apoptosis assays were performed using same colon cancer cell lines. Furthermore, a significantly higher percentage of cell death was observed in the HCT-116 samples co-incubated with GMS515(pK5079) and GMS410(pK5079) than the control strain GMS409 (pK5079) (FIG. 4A-4B). Collectively, the data suggest that the self-eradicating TRAIL-delivering GMS strains with reprogrammed chemotaxis systems hold remarkable cancer cell-killing ability.

Reprogrammed GMS Suppress Tumor Growth In Vivo

The engineered TRAIL-delivering GMS strains with reprogrammed chemotaxis system, displaying multiple cancer-killing features, have the potential to function as cancer therapeutics. Therefore, the impact of reprogrammed GMS-based therapy on tumor growth, following intra-tumor injection, was evaluated in an allograft colon cancer mouse model. The CT-26 cells were subcutaneously (SQ) injected into the flank area of BALB/c mice. First, the colonization of GMS strains in tumor versus spleen was determined nine days post-intratumoral injection (IT) of $10^8$ CFU bacteria. We found that the reprogrammed GMS410(pK5079) and GMS515(pK5079) strains preferably accumulated in the tumors, after injection of bacteria into the tumors on the mice, growing the bacterial density up to 5,000-13,000 times higher comparing to the density of bacteria found in the spleen. In contrast, strain GMS409(pK5079) without chemoreceptor modification selectively accumulated in *Salmonella* preferred colonization organ, spleen. These data suggested that reprogrammed chemotaxis system in GMS410(pK5079) and GMS515(pK5079) increased their capacity of tumor specific accumulation that is a key safety feature required for efficient *Salmonella*-based cancer therapy. We then tested whether the GMS strains specifically accumulated in tumor would suppress tumor growth. Phosphate-buffered saline (PBS), GMS409(pK5079), GMS410 (pK5079), and GMS515(pK5079) were administrated by IT injection. The tumor sizes were measured every three days post-IT injection of bacteria. The tumor size of mice treated with GMS410(pK5079) or GMS515(pK5079) was significantly smaller than that treated with PBS or control strain GMS409(pK5079) after three days following IT injection. Moreover, both GMS410(pK5079) and GMS515(pK5079) treatments prolonged the lifespan of tumor-bearing mice (FIG. 4A). The lifespan of tumor-bearing mice was significantly prolonged, which was correlated with suppression of tumor growth, was ascribed to tumor-navigating GMSmediated oncolysis. To test the hypothesis, immunochemistry staining of Ki67 (an indicator of cancer cell proliferation) and TUNEL (terminal deoxynucleotidyl transferase dUTP nick end-labeling to detect DNA fragmentation as a hallmark of apoptosis) assays were carried out. It was found that much more Ki67 positive cancer cells were present in the PBS and GMS409(pK5079)-treated tumor samples comparing to the tumor samples from the groups treated with GMS410(pK5079) or GMS515(pK5079). Meanwhile, more apoptotic cells were observed in the tumor sections treated with GMS410(pK5079) or GMS515(pK5079) than in the PBS- or control strain-treated tumors (FIG. 4B).

Figures 5A, 5B:
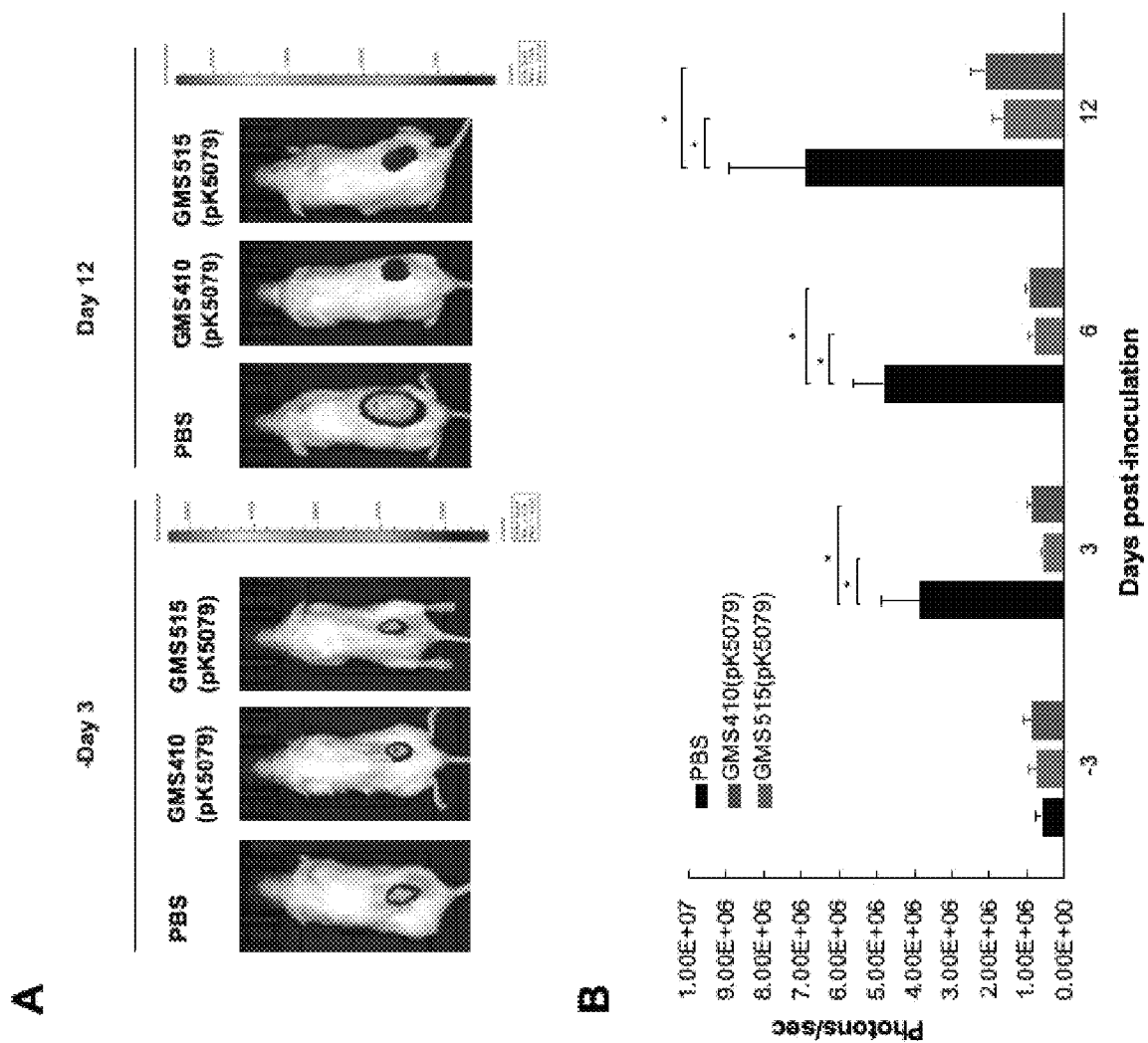
FIGS. 5A-5B demonstrate that reprogrammed GMS strains suppressed tumor growth in HCT-116 SQ tumor model in vivo. A. A set of representative live imaging of NSG™ mice with SQ injected HCT-116 cells captured before and after IT injections of PBS or GMS strain, as indicated. B. Luciferase activities of tumor cells from NSG™ mice before and after GMS strain IT injections were analyzed. The error bar indicates SEM. (n=6, *p<0.05). Experiments were repeated independently three times.

We further evaluated the efficacy of strains GMS410 (pK5079) and GMS515(pK5079) on cancer therapy in vivo using a human colon cancer HCT-116 cell xenograft mouse model. HCT-116 cells, which stably express luciferases, were subcutaneously injected into the flank area of immunocompromised NOD. Cg-Prkdcscid Il2rgtm1Wjl/SzJ (NSG™) mice. PBS, GMS410(pK5079), and GMS515 (pK5079) were IT injected into the NSG™ mice carrying tumors. The tumor growth was monitored through measuring cancer cell luciferase activity using a live imaging system following IT injection. As shown in FIGS. 5A-5B, the tumor luciferase activity of mice treated with GMS410 (pK5079) or GMS515(pK5079) is significantly lower than that in the control tumors (PBS-treated), suggesting that GMS410(pK5079) and GMS515(pK5079) inhibited HCT-116 cancer cell growth in vivo. In addition, Ki67 staining demonstrated that the proliferated cancer cells are much less in tumors treated with GMS410(pK5079) or GMS515 (pK5079) than that in the tumors treated with PBS, which confirmed that GMS410(pK5079) and GMS515(pK5079) were also able to inhibit human colon cancer cell growth in vivo. Furthermore, TUNEL assays showed more apoptotic cells in the tumor sections treated with GMS410(pK5079) or GMS515(pK5079) than that in PBS-treated tumor sections. Taken together, these observations suggested that reprogramming of chemotaxis system was an essential component of GMS anti-cancer effect and the self-eradicating GMS could effectively deliver TRAIL into the tumor microenvironment, and trigger *Salmonella*- and TRAIL-mediated tumor cell death.

Figures 6A, 6B, 6C:
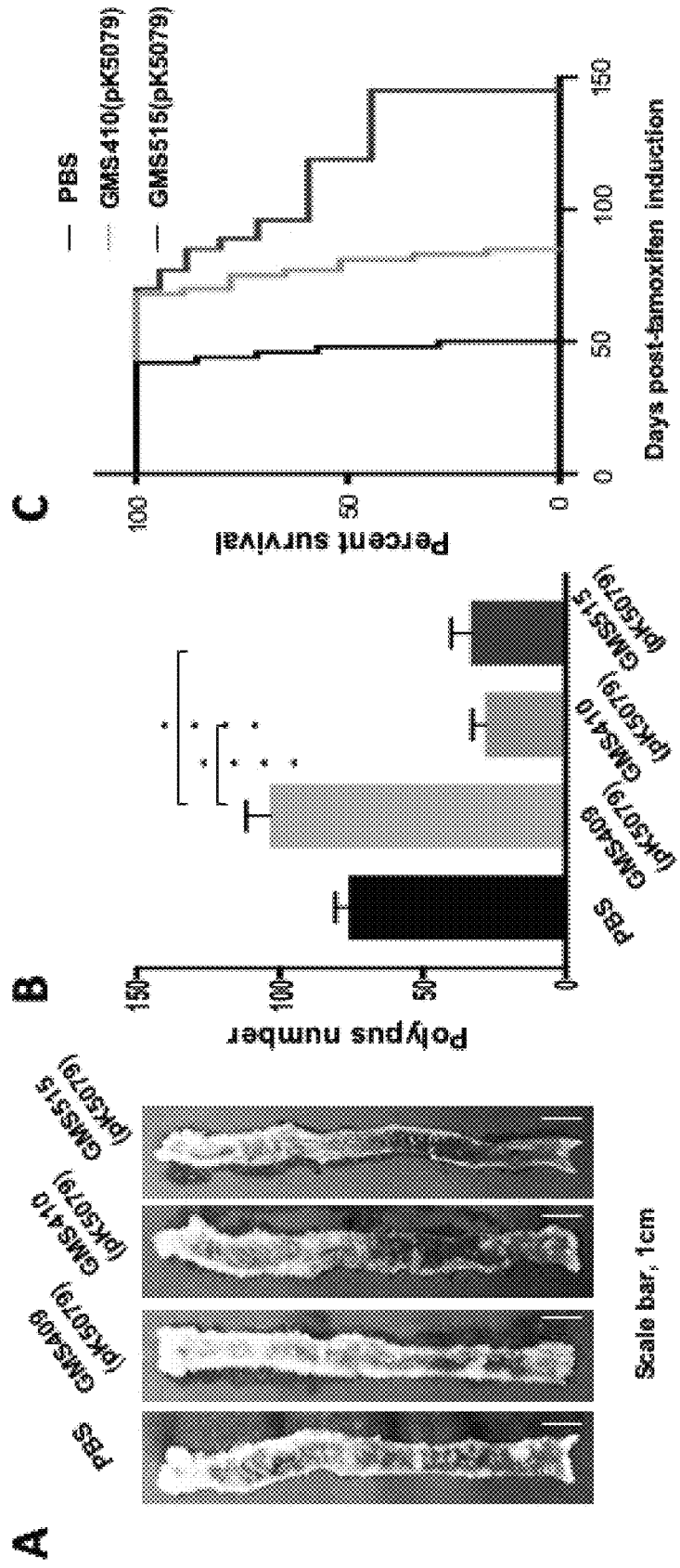
FIGS. 6A-6C demonstrate that reprogrammed GMS strains suppressed tumor progression by promoting cancer cell-killing in a transgenic colon tumor mouse model. A. The representative image of the colon from t-APC mice orally inoculated with PBS or GMS strains, as indicated. B. Numbers of polyps from colons of t-APC mice treated with PBS or GMS strains, as indicated (n=8). C. Survival fraction curves of t-APC mice orally treated with PBS or GMS strains 3 times at 10 days interval (n=7).
Figure 7:
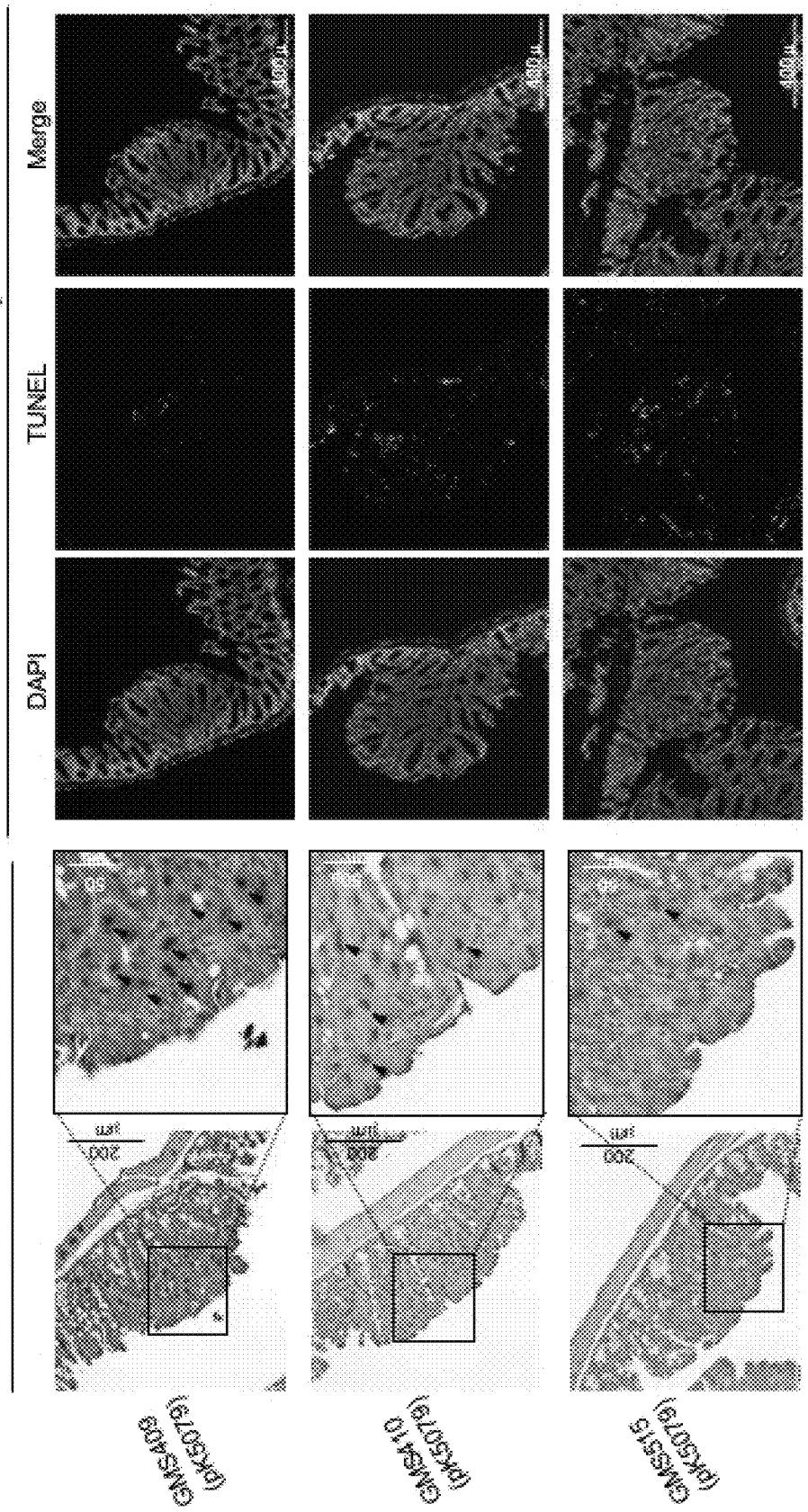
FIG. 7 demonstrates that reprogrammed GMS strains promoted cancer cell-killing in a transgenic colon tumor mouse model. The representative *Salmonella* staining (left, dark brown) in polypus from colons and rectums of tAPC mice treated with PBS or GMS strains, as indicated. TUNEL staining (right, green).

Evaluation of Reprogrammed GMS Strains using a Transgenic Colon Tumor Mouse Model In addition to allograft and xenograft subcutaneous tumor models, we evaluated our GMS strains in a transgenic Apc$^{flox/flox}$CDX2-CRE colon tumor mouse model, which mimic human FAP associated colorectal cancer and sporadic colorectal cancer. Ten days after tamoxifen induction, mice were orally inoculated with PBS, GMS409(pK5079), GMS410(pK5079), and GMS515(pK5079). Tumors in the colons and rectums were counted 10 days post-GMS treatment. As shown in FIGS. 6A-6B, the number of polyps is significantly less in the mice treated with either GMS410 (pK5079) or GMS515(pK5079), compared to the number of polyps of the tamoxifen inducted Apc$^{flox/flox}$CDX2-CRE mice treated with GMS410(pK5079) and GMS515(pK5079) was dramatically increased when compared with the control group. In addition, more positive anti-*Salmonella* immunostaining was observed in the intestinal polyps treated with GMS410(pK5079) and GMS515(pK5079) strains than that in the samples treated with control strain GMS409(pK5079) (FIG. 7). These results suggest that the reprogramming the chemotaxis system enables GMS410(pK5079) and GMS515 (pK5079) to navigate and colonize in tumor tissue following oral inoculation. Furthermore, a TUNEL assay was performed to detect apoptotic cells in the colon polypus. More apoptotic cells were discovered in polypus from the mice treated with GMS410(pK5079) and GMS515(pK5079) than that in the polypus from the mice treated with control GMS409(pK5079) (FIG. 7). Overall, these data further demonstrate that GMS410(pK5079) and GMS515(pK5079) are able to navigate to the tumor and efficiently induce tumor cell apoptosis in vivo.

Figure 8A:
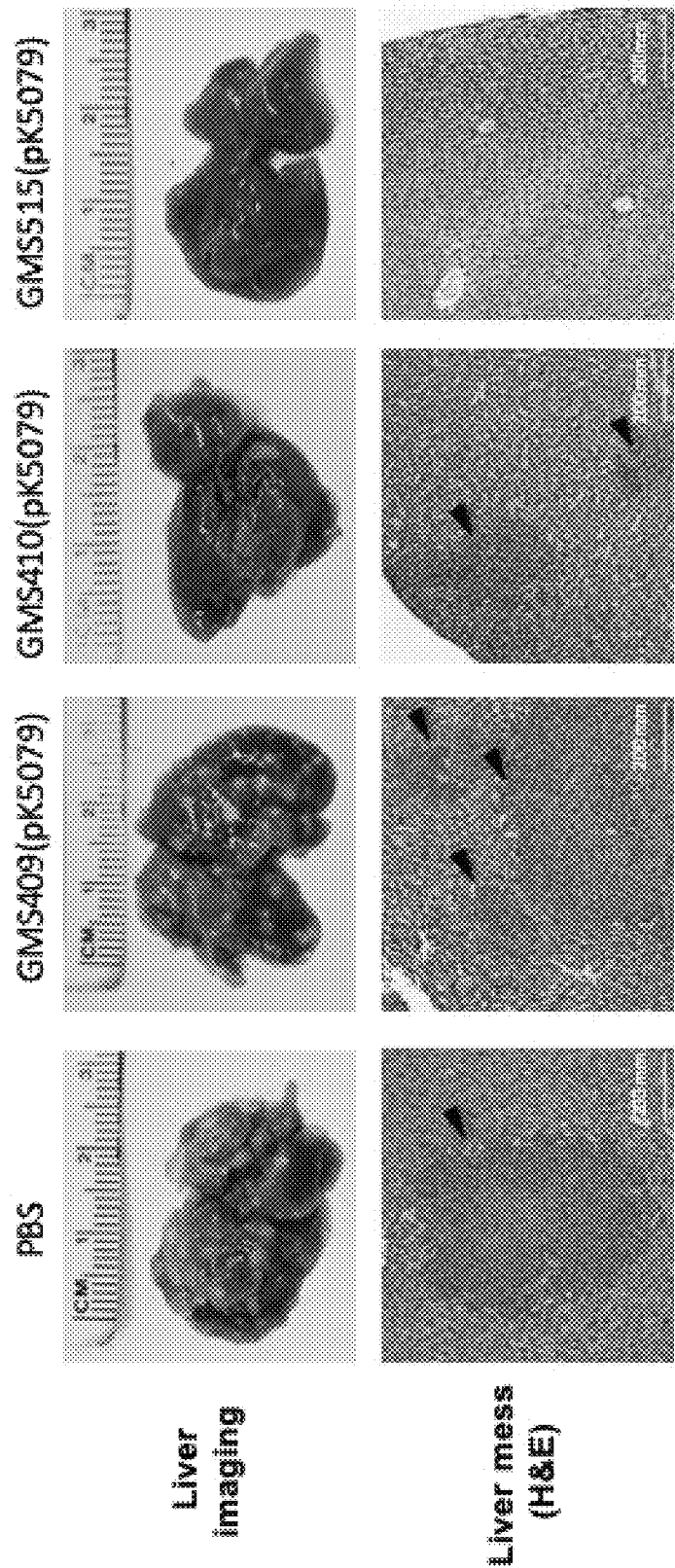
FIGS. 8A-8B demonstrate that reprogrammed GMS strains inhibit liver metastasis in an orthotopic human colon cancer mouse model. A. Representative imaging of liver metastasis (top) and liver section H&E staining (bottom) of the mice treated with PBS or GMS strains, as indicated. B. Numbers of liver metastatic tumors in mice treated with PBS or GMS strains, as indicated (n=12, ***p<0.001).
Figure 8B:
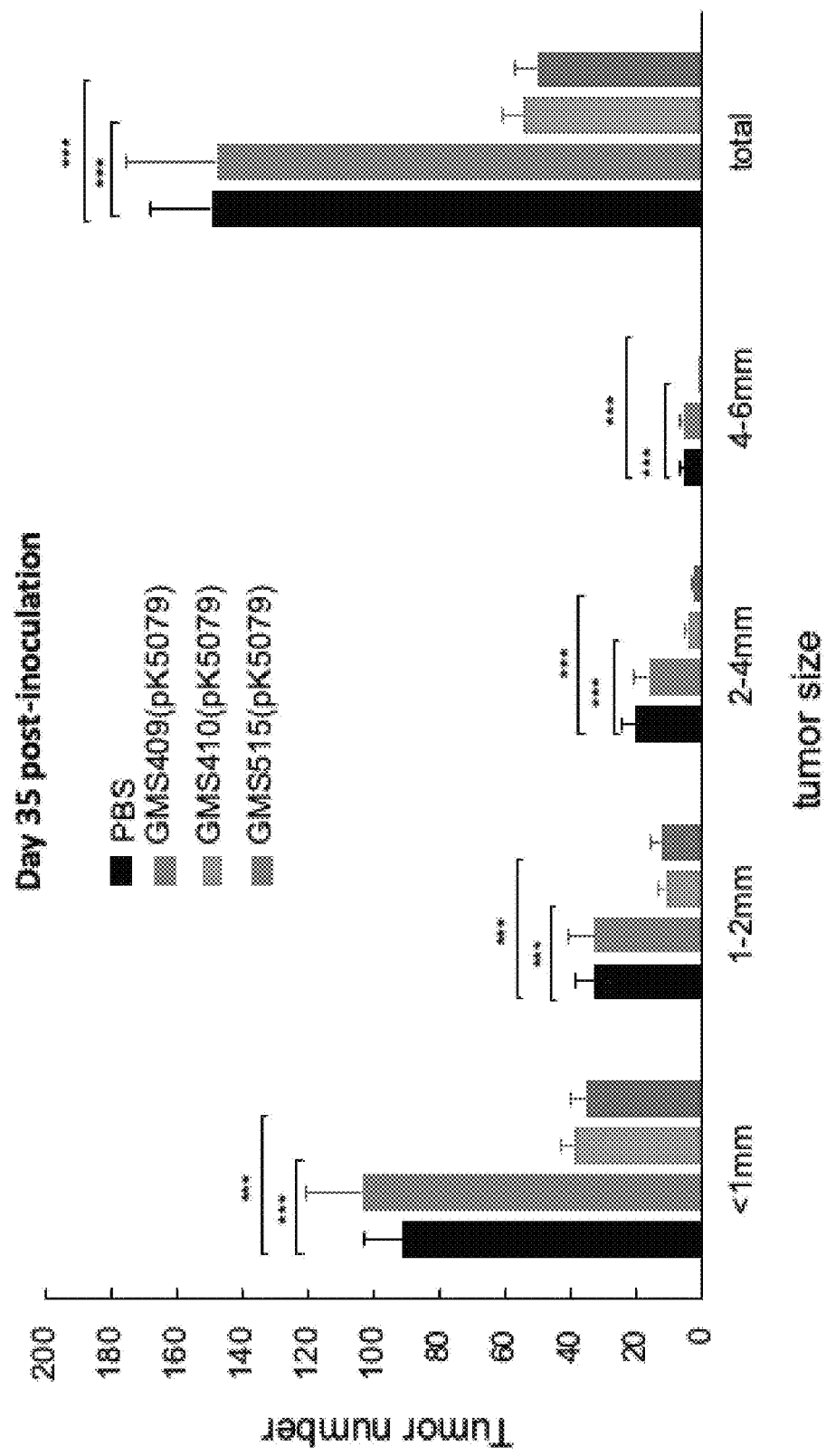

Reprogrammed GMS Strains-Based Therapy for Metastatic Cancer in an Orthotopic Xenograft Mouse Model Colorectal cancer is one of the leading causes of cancer mortality because of its metastasis. Liver is the most common organ for colon cancer metastasis. To investigate whether GMS410(pK5079) and GMS515(pK5079) are able to inhibit liver metastasis from orthotopically implanted colon cancer, the HCT-116 cells expressing luciferase were injected into the cecum wall of NSG™ mice. At day 7 post-surgery, mice were orally inoculated with PBS, GMS409(pK5079), GMS410(pK5079), or GMS515 (pK5079) once per week for 5 weeks. Tumor growth and metastasis were monitored using a live imaging system (FIG. 8A). Metastatic tumor number and size were analyzed at week 5 post-inoculation (FIG. 8B). As shown in FIGS. 8A-8B, colon cancer cells grew from cecum and metastasized to adjacent tissue and distant organ liver in the groups treated with PBS and GMS409(pK5079). However, much less local and distance metastasis was observed in the mice treated with GMS410(pK5079) or GMS515(pK5079). These data indicate that both GMS410(pK5079) and GMS515(pK5079) are capable of reducing tumor metastasis.

Discussion

Despite many advances in conventional methods such as chemo- and radiation-therapy, cancer treatment is still far from optimal. Current cancer therapies frequently encounter challenges including nonspecific systemic distribution of antitumor agents, inadequate drug concentrations reaching the tumor site, intolerable cytotoxicity and development of multiple drug resistance. As with any cancer therapy, the key issue is to achieve the desired concentration of the therapeutic agent specifically in tumor sites, thereby destroying cancerous cells while minimizing damage to normal cells. Bacterial cancer therapies offer unique features that can overcome these obstacles. However, intrinsic bacterial toxicity and tumor-targeting efficiency are two major concerns for the bacterial approach in cancer therapy. We report here that we have now address the concerns by constructing GMS strains with enhanced chemotaxis system that are attracted by tumor released small molecules to confer tumor-navigating feature. Moreover, the regulated delayed attenuation and programmed self-eradicating features designed into these *S. typhimurium* strains enable them to efficiently colonize in tumors and allow release of a target agent (e.g., a tumoricidal protein such as TRAIL, a protein altering tumor metabolism) after cell lysis. As proof of concept, we have demonstrated that the genetically engineered tumor navigating and self-eradicating GMS410(pK5079) and GMS515(pK5079) strains not only improve the safety of cancer treatment, but also efficiently target tumor tissue and release a target agent into the tumor tissues to significantly affect tumor growth and extend the survival rate in both allograft and xenograft colon cancer mouse models. We also validate the efficacy of anti-cancer metastasis using *Salmonella* based-cancer therapies in the orthotopic human colon cancer xenograft mouse model created through cecum wall surgical microinjection, which drives tumor foci to the most relevant metastatic sites observed in humans. Most importantly, orally administrated GMS410(pK5079) and GMS515(pK5079) successfully achieved metastasis blockage in such mouse models. In addition, we are the first to evaluate *Salmonella*-based cancer therapeutics in an inducible APC gene mutation mouse model, which can better mimic human familial adenomatous polyposis disease. The results proved that GMS410(pK5079) and GMS515(pK5079) strains effectively suppressed tumor progression. As such, these GMS strains show tremendous potential, either alone or in combination with other treatments, to make an important contribution in cancer therapy.

The present disclosure has described one or more preferred embodiments, and it should be appreciated that many equivalents, alternatives, variations, and modifications, aside from those expressly stated, are possible and within the scope of the disclosure.

We claim:

1. A genetically modified tumoricidal *Salmonella* bacterium, wherein the bacterium is a self-eradicating, genetically modified χ3761 *Salmonella* bacterium comprising ΔP$_{murA25}$::TT araC P$_{BAD}$ murA, Δ(wcaM-wca)-8 ΔrelA198::araC P$_{BAD}$ lacITT, Δ(araC P$_{BAD}$)-18::P22 PR araBAD, ΔpagP81::P$_{lpp}$ lpxE, ΔendA1123 ΔP$_{tar}$::P$_{trc\ \Delta lacO888}$ tar, ΔP$_{tsr}$::P$_{trc\ \Delta lacO888}$ tsr, Δtrg, ΔpvkA, and ΔpykF, wherein the bacterium comprises a lysis vector pYA3681 expressing murA in the presence of arabinose, the lysis vector comprising pBR ori araC* P$_{BAD}$ SD-GTG asdA SD-GTG murA P22 P$_R$ anti-sense mRNA.

2. A method of treating a cancer or cancer-associated condition in a subject in need thereof, the method comprising administering a genetically modified tumoricidal *Salmonella* bacterium of claim 1 to the subject, whereby the genetically modified tumoricidal *Salmonella* bacterium treats the cancer or cancer-associated condition.

3. The method of claim 2, wherein administering comprises oral administration or intra-tumoral injection of the genetically modified tumoricidal *Salmonella* bacterium.

4. The genetically modified tumoricidal Salmonella bacterium of claim 1, further comprising:

ΔsseL and ΔspvD,

ΔsseL and ΔssrAB, or

ΔsseL, ΔspvD, and ΔssrAB.

5. A method of treating a cancer or cancer-associated condition in a subject in need thereof, the method comprising administering a genetically modified tumoricidal *Salmonella* bacterium according to claim 4 to the subject, whereby the genetically modified tumoricidal *Salmonella* bacterium treats the cancer or cancer-associated condition.

6. The method of claim 5, wherein administering comprises oral administration or intra-tumoral injection of the genetically modified tumoricidal *Salmonella* bacterium.

7. The genetically modified tumoricidal *Salmonella* bacterium of claim 1, further comprising ΔsseL (GMS530 (pYA3681)).

8. The genetically modified tumoricidal *Salmonella* bacterium of claim 1, further comprising ΔspvD (GMS531 (pYA3681)).

9. The genetically modified tumoricidal *Salmonella* bacterium of claim 1, further comprising ΔssrAB (GMS532 (pYA3681)).

10. A method of treating a cancer or cancer-associated condition in a subject in need thereof, the method comprising administering a genetically modified tumoricidal *Salmonella* bacterium according to claim 7 to the subject, whereby the genetically modified tumoricidal *Salmonella* bacterium treats the cancer or cancer-associated condition.

11. The method of claim 10, wherein administering comprises oral administration or intra-tumoral injection of the genetically modified tumoricidal *Salmonella* bacterium.

12. A method of treating a cancer or cancer-associated condition in a subject in need thereof, the method comprising administering a genetically modified tumoricidal *Salmonella* bacterium according to claim 8 to the subject, whereby the genetically modified tumoricidal *Salmonella* bacterium treats the cancer or cancer-associated condition.

13. The method of claim 12, wherein administering comprises oral administration or intra-tumoral injection of the genetically modified tumoricidal *Salmonella* bacterium.

14. A method of treating a cancer or cancer-associated condition in a subject in need thereof, the method comprising administering a genetically modified tumoricidal *Salmonella* bacterium according to claim 9 to the subject, whereby the genetically modified tumoricidal *Salmonella* bacterium treats the cancer or cancer-associated condition.

15. The method of claim 14, wherein administering comprises oral administration or intra-tumoral injection of the genetically modified tumoricidal *Salmonella* bacterium.

* * * * *

SEQUENCE LISTING

```
<160> NUMBER OF SEQ ID NOS: 16

<210> SEQ ID NO 1
<211> LENGTH: 1531
<212> TYPE: DNA
<213> ORGANISM: Artificial Sequence
<220> FEATURE:
<223> OTHER INFORMATION: Synthetic- ptsG deletion-insertion mutation
<220> FEATURE:
<221> NAME/KEY: misc_feature
<222> LOCATION: (1)..(94)
<223> OTHER INFORMATION: Promoter: Ptrc with lacO deletion

<400> SEQUENCE: 1
attctgaaat gagctgttga caattaatca tccggctcgt ataatgtgta gatgcgtagg      60
cacctgttac gacgaaccac acaggaaaca gaccatgttt aagaatgcat ttgctaacct     120
gcaaaaggtc ggtaaatcgc tgatgctgcc ggtatccgta ctccctatcg caggtatcct     180
gctgggtgtc ggttccgcta acttcagctg gctgccagcc gttgtatcgc acgttatggc     240
agaagcgggc ggatctgttt ttgccaatat gccgctgatt ttcgctatcg gcgtggcgtt     300
gggcttcacc aacaacgacg gcgtttcggc tctggcggcg gtagtcgcgt atggcatcat     360
ggtgaaaacc atggctgtgg ttgcgccgct ggttctgcat ttacctgctg aagagatcgc     420
cgctaaacac cttgctgata cgggtgttct cggggggatt atctccggtg caatcgcagc     480
gtatatgttt aaccgcttct accgtatcaa actgcctgag tatctgggct tctttgcggg     540
caaacgcttc gtgccgatca tttcgggtct ggccgctatt tttaccggtg tggtgctgtc     600
tttcgtatgg ccgccaatcg gtacggctat ccaggcgttc tcgcagtggg cggcttatca     660
gaacccggtt gtcgcgtttg gtatttacgg ttttatcgag cgttgcctgg tgccgtttgg     720
tctgcatcat atctggaacg ttcctttcca gatgcagatc ggcgaatata ccaacgcagc     780
gggtcaggta ttccacggcg acattccgcg ctatatggcg ggcgacccga cggcaggtat     840
gttgtctggc ggcttcctgt tcaaaatgta cggtctgccg gctgcggcca ttgctatctg     900
gcactctgct aaaccggaaa accgcgcaaa agtgggcggt atcatgattt ccgccgcgct     960
gacctcgttt ttgacgggta ttaccgagcc tatcgagttc tccttcatgt tcgtggcgcc    1020
gatcctgtac attattcacg cgattctggc aggtctggca ttcccgatct gtatcctgct    1080
ggggatgcgt gacggtacgt cgttctccca cggtctgatc gactttatcg tgctgtccgg    1140
taacagcagc aaattgtggc tgttcccgat tgttggcgcc ggttatgcga ttgtgtacta    1200
caccgtgttc cgcgtgctga tcaaagcgtt ggatctgaaa acgccgggtc gtgaagacac    1260
tactgatgac gcaaaagcgg gggcgaccag cgaaatggcg ccggctttgg ttgcggcgtt    1320
tggcggtaaa gagaacatca ctaacctgga tgcctgtatc acgcgtctgc gcgtgagcgt    1380
agccgatgta gcgaaagtgg atcaggctgg cctgaagaaa ctgggcgcgg caggcgttgt    1440
```

-continued

```
cgtcgcgggt tccggcgttc aggctatttt cggtacgaaa tccgataacc tgaaaacgga    1500
aatggatgag tacatccgta acagctaatg a                                   1531
```

<210> SEQ ID NO 2
<211> LENGTH: 6238
<212> TYPE: DNA
<213> ORGANISM: Artificial Sequence
<220> FEATURE:
<223> OTHER INFORMATION: Synthetic- plasmid pK4960: suicide vector for construction of ptsG deletion-insertion mutation

<400> SEQUENCE: 2

```
cgcgtttccg agaaccgcgc gaacgacatg gagcggcacg cgggcgtgga aagcctggtc      60
ggctggatcg gcacgatgcg tccggcgtag aggatctgaa gatccagcag ttcaacctgt     120
tgatagtacg tactaagctc tcatgtttca cgtactaagc tctcatgttt aacgtactaa     180
gctctcatgt ttaacgaact aaaccctcat ggctaacgta ctaagctctc atggctaacg     240
tactaagctc tcatgtttca cgtactaagc tctcatgttt gaacaataaa attaatataa     300
atcagcaact aaatagcct ctaaggtttt aagttttata agaaaaaaaa gaatatataa      360
ggcttttaaa gcttttaagg tttaacggtt gtggacaaca agccagggat gtaacgcact     420
gagaagccct tagagcctct caaagcaatt ttcagtgaca caggaacact taacggctga     480
catgggaatt ctgatccttt ttaacccatc acatatacct gccgttcact attatttagt     540
gaaatgagat attatgatat tttctgaatt gtgattaaaa aggcaacttt atgcccatgc     600
aacagaaact ataaaaaata cagagaatga aagaaacag atagattttt tagttcttta     660
ggcccgtagt ctgcaaatcc ttttatgatt ttctatcaaa caaagagga aaatagacca     720 gttgcaatcc aaacgagagt ctaatagaat gaggtcgaaa agtaaatcgc gcgggtttgt     780
tactgataaa gcaggcaaga cctaaaatgt gtaaagggca aagtgtatac tttggcgtca     840
ccccttacat attttaggtc tttttttatt gtgcgtaact aacttgccat cttcaaacag     900
gagggctgga agaagcagac cgctaacaca gtacataaaa aaggagacat gaacgatgaa     960
catcaaaaag tttgcaaaac aagcaacagt attaacctt actaccgcac tgctggcagg    1020
aggcgcaact caagcgtttg cgaaagaaac gaaccaaaag ccatataagg aaacatacgg    1080
catttcccat attacacgcc atgatatgct gcaaatccct gaacagcaaa aaatgaaaa    1140 atatcaagtt cctgagttcg attcgtccac aattaaaaat atctcttctg caaaaggcct    1200
ggacgtttgg gacagctggc cattacaaaa cgctgacggc actgtcgcaa actatcacgg    1260
ctaccacatc gtctttgcat tagccggaga tcctaaaaat gcggatgaca catcgattta    1320
catgttctat caaaaagtcg gcgaaacttc tattgacagc tggaaaaacg ctggccgcgt    1380 cttttaaagac agcgacaaat tcgatgcaaa tgattctatc ctaaaagacc aaacacaaga    1440
atggtcaggt tcagccacat ttacatctga cggaaaaatc cgtttattct acactgattt    1500
ctccggtaaa cattacggca acaaacact gacaactgca caagttaacg tatcagcatc    1560
agacagctct ttgaacatca acggtgtaga ggattataaa tcaatctttg acggtgacgg    1620
aaaaacgtat caaaatgtac agcagttcat cgatgaaggc aactacagct caggcgacaa    1680
ccatacgctg agagatcctc actacgtaga agataaaggc cacaaatact tagtatttga    1740
agcaaacact ggaactgaag atggctacca aggcgaagaa tctttatta acaaagcata    1800 ctatggcaaa agcacatcat tcttccgtca agaaagtcaa aaacttctgc aaagcgataa    1860
aaaacgcacg gctgagttag caaacggcgc tctcggtatg attgagctaa acgatgatta    1920
```

```
cacactgaaa aaagtgatga aaccgctgat tgcatctaac acagtaacag atgaaattga   1980
acgcgcgaac gtctttaaaa tgaacggcaa atggtatctg ttcactgact cccgcggatc   2040
aaaaatgacg attgacggca ttacgtctaa cgatatttac atgcttggtt atgtttctaa   2100
ttctttaact ggcccataca agccgctgaa caaaactggc cttgtgttaa aaatggatct   2160
tgatcctaac gatgtaacct ttacttactc acacttcgct gtacctcaag cgaaaggaaa   2220
caatgtcgtg attacaagct atatgacaaa cagaggattc tacgcagaca aacaatcaac   2280
gtttgcgccc agcttcctgc tgaacatcaa aggcaagaaa acatctgttg tcaaagacag   2340
catccttgaa caaggacaat taacagttaa caaataaaaa cgcaaaagaa atgccgata    2400
tcctattggc atttctttt atttcttatc aacataaagg tgaatcccat atgaactata   2460
taaaagcagg caaatggcta accgtattcc taaccttttg gtaatgactc caacttattg   2520
atagtgtttt atgttcagat aatgcccgat gactttgtca tgcagctcca ccgattttga   2580
gaacgacagc gacttccgtc ccagccgtgc caggtgctgc ctcagattca ggttatgccg   2640
ctcaattcgc tgcgtatatc gcttgctgat tacgtgcagc tttcccttca ggcgggattc   2700
atacagcggc cagccatccg tcatccatat caccacgtca aagggtgaca gcaggctcat   2760
aagacgcccc agcgtcgcca tagtgcgttc accgaatacg tgcgcaacaa ccgtcttccg   2820
gagactgtca tacgcgtaaa acagccagcg ctggcgcgat ttagccccga catagcccca   2880
ctgttcgtcc atttccgcgc agacgatgac gtcactgccc ggctgtatgc gcgaggttac   2940
cgactgcggc ctgagttttt taagtgacgt aaaatcgtgt tgaggccaac gcccataatg   3000
cgggctgttg cccggcatcc aacgccattc atggccatat caatgatttt ctggtgcgta   3060
ccgggttgag aagcggtgta agtgaactgc atgaattccc gggagagctc gatatcgcat   3120
gcggtacctc tagaagaagc ttcgcggtaa agagaaccag cctgcgatgg tacgcgacgt   3180
cgcagaatat atggcggtat tgaaaggggt tgccgttgaa gaactggcgc agatcaccac   3240
cgataacttt gctcgcctgt tccatattga cgcgtctcgc ctgtcatcaa tccgttaaac   3300
gagttttttt aaagctcgta attaataaac aaaacgcgta agttcaccg ccacaaaagg   3360
ggcggtgagc gagcttatgg aaacattcgg aaactcattt tggcagaatg tgatactttt   3420
taggctatct ggcgctgaaa cgtgatagcc gtcaaacaaa atcagacgta tttatttac    3480
tctgtgtaat aaataaaagg gcacttagat gtcctgtcca cggcggggtt ctcccccctc   3540
gccaatgcgt gagaacgtag aaaagcacaa atactcagga gcactctcaa ttattctgaa   3600
atgagctgtt gacaattaat catccggctc gtataatgtg tagatgcgta ggcacctgtt   3660
acgacgaacc acacaggaaa cagaccatgt ttaagaatgc atttgctaac ctgcaaaagg   3720
tcggtaaatc gctgatgctg ccggtatccg tactccctat cgcaggtatc ctgctgggtg   3780
tcggttccgc taacttcagc tggctgccag ccgttgtatc gcacgttatg cagaagcgg    3840
gcggatctgt ttttgccaat atgccgctga ttttcgctat cggcgtggcg ttgggcttca   3900
ccaacaacga cggcgtttcg gctctggcgg cggtagtcgc gtatggcatc atggtgaaaa   3960
ccatggctgt ggttgcgccg ctggttctgc atttacctgc tgaagagatc gccgctaaac   4020
accttgctga tacgggtgtt ctcggggga ttatctccgg tgcaatcgca gcgtatatgt   4080
ttaaccgctt ctaccgtatc aaactgcctg agtatctggg cttctttgcg ggcagaattc   4140
cggatgagca ttcatcaggc gggcaagaat gtgaataaag gccggataaa acttgtgctt   4200
attttctttt acggtcttta aaaggccgt aatatccagc tgaacggtct ggttatagg    4260
acattgagca actgactgaa atgcctcaaa atgttcttta cgatgccatt gggatatatc   4320
```

```
aacggtggta tatccagtga tttttttctc cattttagct tccttagctc ctgaaaatct    4380
cgataactca aaaatacgc ccggtagtga tcttatttca ttatggtgaa agttggaacc    4440
tcttacgtgc cgatcaacgt ctcattttcg ccaaaagttg gcccagggct tcccggtatc    4500
aacagggaca ccaggattta tttattctgc gaagtgatct tccgtcacag gtattagggc    4560
ccgatccttt tgtccggtg ttgggttgaa ggtgaagccg gtcggggccg cagcggggc     4620 cggcttttca gccttgcccc cctgcttcgg ccgccgtggc tccggcgtct tgggtgccgg    4680
cgcgggttcc gcagccttgg cctgcggtgc gggcacatcg gcgggcttgg ccttgatgtg    4740
ccgcctggcg tgcgagcgga acgtctcgta ggagaacttg accttcccg tttcccgcat     4800 gtgctcccaa atggtgacga gcgcatagcc ggacgctaac gccgcctcga catccgccct    4860
caccgccagg aacgcaaccg cagcctcatc acgccggcgc ttcttggccg cgcgggattc    4920
aacccactcg gccagctcgt cggtgtagct ctttggcatc gtctctcgcc tgtcccctca    4980
gttcagtaat ttcctgcatt tgcctgtttc cagtcggtag atattccaca aaacagcagg    5040
gaagcagcgc ttttccgctg cataaccctg cttcggggtc attatagcga ttttttcggt    5100
atatccatcc ttttcgcac gatatacagg attttgccaa aggggtcgtg tagactttcc     5160
ttggtgtatc caacggcgtc agccgggcag gataggtgaa gtaggcccac ccgcgagcgg    5220
gtgttccttc ttcactgtcc cttattcgca cctggcggtg ctcaacggga atcctgctct    5280
gcgaggctgg ccggctaccg ccggcgtaac agatgagggc aagcggatgg ctgatgaaac    5340
caagccaacc aggaagggca gcccacctat caaggtgtac tgccttccag acgaacgaag    5400
agcgattgag gaaaaggcgg cggcggccgg catgagcctg tcggcctacc tgctggccgt    5460
cggccagggc tacaaaatca cgggcgtcgt ggactatgag cacgtccgcg agctggcccg    5520
catcaatggc gacctgggcc gcctgggcgg cctgctgaaa ctctggctca ccgacgaccc    5580
gcgcacggcg cggttcggtg atgccacgat cctcgccctg ctggcgaaga tcgaagagaa    5640
gcaggacgag cttggcaagg tcatgatggg cgtggtccgc ccgagggcag agccatgact    5700
tttttagccg ctaaaacggc cggggggtgc gcgtgattgc caagcacgtc cccatgcgct    5760
ccatcaagaa gagcgacttc gcggagctgg tgaagtacat caccgacgag caaggcaaga    5820
ccgagcgcct gggtcacgtg cgcgtcacga actgcgaggc aaacaccctg cccgctgtca    5880
tggccgaggt gatggcgacc cagcacggca cacccgttc cgaggccgac aagacctatc     5940
acctgctggt tagcttccgc gcgggagaga gcccgacgc ggagacgttg cgcgcgattg      6000
aggaccgcat ctgcgctggg cttggcttcg ccgagcatca gcgcgtcagt gccgtgcatc    6060
acgacaccga caacctgcac atccatatcg ccatcaacaa gattcacccg acccgaaaca    6120
ccatccatga gccgtatcgg gcctaccgcg ccctcgctga cctctgcgcg acgctcgaac    6180
gggactacgg gcttgagcgt gacaatcacg aaacgcggca gcgcgtttcc gagaaccg     6238
```

<210> SEQ ID NO 3
<211> LENGTH: 6146
<212> TYPE: DNA
<213> ORGANISM: Artificial Sequence
<220> FEATURE:
<223> OTHER INFORMATION: Synthetic- plasmid pK4961: suicide vector for
      construction of pykA deletion mutation

<400> SEQUENCE: 3

```
cgcgtttccg agaaccgcgc gaacgacatg gagcggcacg cgggcgtgga aagcctggtc      60
ggctggatcg gcacgatgcg tccggcgtag aggatctgaa gatccagcag ttcaacctgt     120
```

```
tgatagtacg tactaagctc tcatgtttca cgtactaagc tctcatgttt aacgtactaa       180
gctctcatgt ttaacgaact aaaccctcat ggctaacgta ctaagctctc atggctaacg       240
tactaagctc tcatgtttca cgtactaagc tctcatgttt gaacaataaa attaatataa       300
atcagcaact taaatagcct ctaaggtttt aagttttata agaaaaaaaa gaatatataa       360
ggcttttaaa gcttttaagg tttaacggtt gtggacaaca agccagggat gtaacgcact       420
gagaagccct tagagcctct caaagcaatt ttcagtgaca caggaacact taacggctga       480
catgggaatt ctgatccttt ttaacccatc acatatacct gccgttcact attatttagt       540
gaaatgagat attatgatat tttctgaatt gtgattaaaa aggcaacttt atgcccatgc       600
aacagaaact ataaaaaata cagagaatga aagaaacag atagattttt tagttcttta       660
ggcccgtagt ctgcaaatcc tttatgatt ttctatcaaa caaagagga aaatagacca       720 gttgcaatcc aaacgagagt ctaatagaat gaggtcgaaa agtaaatcgc gcgggtttgt       780
tactgataaa gcaggcaaga cctaaaatgt gtaaagggca aagtgtatac tttggcgtca       840 cccccttacat attttaggtc tttttttatt gtgcgtaact aacttgccat cttcaaacag       900
gagggctgga agaagcagac cgctaacaca gtacataaaa aaggagacat gaacgatgaa       960
catcaaaaag tttgcaaaac aagcaacagt attaaccttt actaccgcac tgctggcagg      1020
aggcgcaact caagcgtttg cgaaagaaac gaaccaaaag ccatataagg aaacatacgg      1080
catttcccat attacacgcc atgatatgct gcaaatccct gaacagcaaa aaatgaaaa      1140 atatcaagtt cctgagttcg attcgtccac aattaaaaat atctcttctg caaaaggcct      1200
ggacgtttgg gacagctggc cattacaaaa cgctgacggc actgtcgcaa actatacgg      1260 ctaccacatc gtctttgcat tagccggaga tcctaaaaat gcggatgaca catcgattta      1320
catgttctat caaaaagtcg gcgaaacttc tattgacagc tggaaaaacg ctggccgcgt      1380
ctttaaagac agcgacaaat tcgatgcaaa tgattctatc ctaaaagacc aaacacaaga      1440
atggtcaggt tcagccacat ttacatctga cggaaaaatc cgtttattct acactgattt      1500
ctccggtaaa cattacggca aacaaacact gacaactgca caagttaacg tatcagcatc      1560
agacagctct ttgaacatca acggtgtaga ggattataaa tcaatctttg acggtgacgg      1620
aaaaacgtat caaaatgtac agcagttcat cgatgaaggc aactacagct caggcgacaa      1680
ccatacgctg agagatcctc actacgtaga agataaaggc cacaaatact tagtatttga      1740
agcaaacact ggaactgaag atggctacca aggcgaagaa tctttatta acaaagcata      1800 ctatggcaaa agcacatcat tcttccgtca agaaagtcaa aaacttctgc aaagcgataa      1860
aaaacgcacg gctgagttag caaacggcgc tctcggtatg attgagctaa acgatgatta      1920
cacactgaaa aaagtgatga aaccgctgat tgcatctaac acagtaacag atgaaattga      1980
acgcgcgaac gtctttaaaa tgaacggcaa atggtatctg ttcactgact cccgcggatc      2040
aaaaatgacg attgacggca ttacgtctaa cgatatttac atgcttggtt atgtttctaa      2100
ttctttaact ggcccataca agccgctgaa caaaactggc cttgtgttaa aaatggatct      2160
tgatcctaac gatgtaacct ttacttactc acacttcgct gtacctcaag cgaaaggaaa      2220
caatgtcgtg attacaagct atatgacaaa cagaggattc tacgcagaca acaatcaac      2280 gtttgcgccc agcttcctgc tgaacatcaa aggcaagaaa acatctgttg tcaaagacag      2340
catccttgaa caaggacaat taacagttaa caaataaaaa cgcaaaagaa atgccgata      2400 tcctattggc atttctttt atttcttatc aacataaagg tgaatcccat atgaactata      2460
```

```
taaaagcagg caaatggcta accgtattcc taaccttttg gtaatgactc caacttattg    2520
atagtgtttt atgttcagat aatgcccgat gactttgtca tgcagctcca ccgattttga    2580
gaacgacagc gacttccgtc ccagccgtgc caggtgctgc ctcagattca ggttatgccg    2640
ctcaattcgc tgcgtatatc gcttgctgat tacgtgcagc tttcccttca ggcgggattc    2700
atacagcggc cagccatccg tcatccatat caccacgtca aagggtgaca gcaggctcat    2760
aagacgcccc agcgtcgcca tagtgcgttc accgaatacg tgcgcaacaa ccgtcttccg    2820
gagactgtca tacgcgtaaa acagccagcg ctggcgcgat ttagccccga catagcccca    2880
ctgttcgtcc atttccgcgc agacgatgac gtcactgccc ggctgtatgc gcgaggttac    2940
cgactgcggc ctgagttttt taagtgacgt aaaatcgtgt tgaggccaac gcccataatg    3000
cgggctgttg cccggcatcc aacgccattc atggccatat caatgatttt ctggtgcgta    3060
ccgggttgag aagcggtgta agtgaactgc atgaattccc gggagagctc gatatcgcat    3120
gcggtacctc tagaagaagc ttatttcgca tactggcaga accaagagcc tggtggaact    3180
ggcgcagttg gcgcgggaaa acgatgcgat ggtgatcgcc ctgacctccg ctggaacgcc    3240
gctggcgcgc gaagccacgc tggccattac cctcgacgta ccggaagata cagacattta    3300
tatgcccatg gtctctcgac ttgctcagct gaccgtgata gatgtgctgg caacgggatt    3360
tactttgcgt cgcggggcaa aattcagaga taacttgaag cgtgtcaagg aagcgctcaa    3420
ggaatcgcgt tttgataaag aattactcat caagagtgat gaccgctaaa agcaataaca    3480
atgttctacc cttttcgtca tccggggacg ttcattttat accgttaagg tttcagaacg    3540
accggatcaa tgttcacgca acaccaagtt gttttagtca acgagtatt acaactcccc     3600
cacgcctgtt catcaggtag tacagggttt gtcagcataa agcctctctt acgagaggct    3660
ttatttatt gatgggataa agatctttac gcttatacgg ctgaatctcg cctggcttgc     3720
gggttttgag cagcttcagg atccaggtgt actgttccgg atgcgggccg acaaaaattt    3780
cgacctcttc gttcatccgt ctggcgatag tgtggtcgtc agccgtgagc agatcgtcca    3840
ttggcgggcg aatctggata gtcaggcgat gcgttttacc attatacacc gggaaaagcg    3900
gtatcacgcg tgcgcggcac actttcatca gccgaccaat gcaggcagc gtcgctttgt     3960
atgtcgcaaa gaaatcaacg aattcactat gctccgggcc gtgatcctgg tccggcaggt    4020
agtaacccca gtagccctga cggaattccg gatgagcatt catcaggcgg gcaagaatgt    4080
gaataaaggc cggataaaac ttgtgcttat ttttctttac ggtctttaaa aaggccgtaa    4140
tatccagctg aacggtctgg ttataggtac attgagcaac tgactgaaat gcctcaaaat    4200
gttctttacg atgccattgg gatatatcaa cggtggtata ccagtgatt ttttctcca     4260
ttttagcttc cttagctcct gaaaatctcg ataactcaaa aaatacgccc ggtagtgatc    4320
ttatttcatt atggtgaaag ttggaacctc ttacgtgccg atcaacgtct catttcgcc    4380
aaaagttggc ccagggcttc ccggtatcaa caggacacc aggatttatt tattctgcga   4440
agtgatcttc cgtcacaggt attagggccc gatcctttt gtccggtgtt gggttgaagg     4500
tgaagccggt cggggccgca gcggggccg gcttttcagc cttgcccccc tgcttcggcc    4560
gccgtggctc cggcgtcttg ggtgccggcg cgggttccgc agccttggcc tgcggtgcgg    4620
gcacatcggc gggcttggcc ttgatgtgcc gcctggcgtg cgagcggaac gtctcgtagg    4680
agaacttgac cttccccgtt tcccgcatgt gctcccaaat ggtgacgagc gcatagccgg    4740
acgctaacgc cgcctcgaca tccgcccctca ccgccaggaa cgcaaccgca gcctcatcac    4800
gccggcgctt cttggccgcg cgggattcaa cccactcggc cagctcgtcg gtgtagctct    4860
```

```
ttggcatcgt ctctcgcctg tccnctcagt tcagtaattt cctgcatttg cctgtttcca    4920
gtcggtagat attccacaaa acagcaggga agcagcgctt ttccgctgca taaccctgct    4980
tcggggtcat tatagcgatt ttttcggtat atccatcctt tttcgcacga tatacaggat    5040
tttgccaaag ggttcgtgta gactttcctt ggtgtatcca acggcgtcag ccgggcagga    5100
taggtgaagt aggcccaccc gcgagcgggt gttccttctt cactgtccct tattcgcacc    5160
tggcggtgct caacgggaat cctgctctgc gaggctggcc ggctaccgcc ggcgtaacag    5220
atgagggcaa gcggatggct gatgaaacca agccaaccag aagggcagc ccacctatca     5280 aggtgtactg ccttccagac gaacgaagag cgattgagga aaaggcggcg gcggccggca    5340
tgagcctgtc ggcctacctg ctggccgtcg gccagggcta caaaatcacg ggcgtcgtgg    5400
actatgagca cgtccgcgag ctggcccgca tcaatggcga cctgggccgc ctgggcggcc    5460
tgctgaaact ctggctcacc gacgacccgc gcacggcgcg gttcggtgat gccacgatcc    5520
tcgccctgct ggcgaagatc gaagagaagc aggacgagct tggcaaggtc atgatgggcg    5580
tggtccgccc gagggcagag ccatgacttt tttagccgct aaaacggccg ggggtgcgc     5640 gtgattgcca agcacgtccc catgcgctcc atcaagaaga cgacttcgc ggagctggtg     5700 aagtacatca ccgacgagca aggcaagacc gagcgcctgg gtcacgtgcg cgtcacgaac    5760
tgcgaggcaa acaccctgcc cgctgtcatg gccgaggtga tggcgaccca gcacggcaac    5820
acccgttccg aggccgacaa gacctatcac ctgctggtta gcttccgcgc gggagagaag    5880
cccgacgcgg agacgttgcg cgcgattgag gaccgcatct gcgctgggct tggcttcgcc    5940
gagcatcagc gcgtcagtgc cgtgcatcac gacaccgaca acctgcacat ccatatcgcc    6000
atcaacaaga ttcacccgac ccgaaacacc atccatgagc cgtatcgggc ctaccgcgcc    6060
ctcgctgacc tctgcgcgac gctcgaacgg gactacgggc ttgagcgtga caatcacgaa    6120
acgcggcagc gcgtttccga gaaccg                                         6146
```

<210> SEQ ID NO 4
<211> LENGTH: 6146
<212> TYPE: DNA
<213> ORGANISM: Artificial Sequence
<220> FEATURE:
<223> OTHER INFORMATION: Synthetic- plasmid pK4962: suicide vector for
      construction of PykF deletion mutation

<400> SEQUENCE: 4

```
cgcgttccg agaaccgcgc gaacgacatg gagcggcacg cgggcgtgga aagcctggtc       60
ggctggatcg gcacgatgcg tccggcgtag aggatctgaa gatccagcag ttcaacctgt     120
tgatagtacg tactaagctc tcatgtttca cgtactaagc tctcatgttt aacgtactaa    180
gctctcatgt ttaacgaact aaaccctcat ggctaacgta ctaagctctc atggctaacg    240
tactaagctc tcatgtttca cgtactaagc tctcatgttt gaacaataaa attaatataa    300
atcagcaact aaatagcct ctaaggtttt aagttttata agaaaaaaaa gaatatataa     360
ggcttttaaa gcttttaagg tttaacggtt gtggacaaca agccagggat gtaacgcact    420
gagaagccct tagagcctct caaagcaatt ttcagtgaca caggaacact taacggctga    480
catgggaatt ctgatccttt ttaacccatc acatatacct gccgttcact attatttagt    540
gaaatgagat attatgatat tttctgaatt gtgattaaaa aggcaacttt atgcccatgc    600
aacagaaact ataaaaaata cagagaatga aagaaacag atagattttt tagttctttta    660 ggcccgtagt ctgcaaatcc ttttatgatt ttctatcaaa caaaagagga aaatagacca    720
```

```
gttgcaatcc aaacgagagt ctaatagaat gaggtcgaaa agtaaatcgc gcgggtttgt    780
tactgataaa gcaggcaaga cctaaaatgt gtaaagggca aagtgtatac tttggcgtca    840
ccccttacat attttaggtc tttttttatt gtgcgtaact aacttgccat cttcaaacag    900
gagggctgga agaagcagac cgctaacaca gtacataaaa aaggagacat gaacgatgaa    960
catcaaaaag tttgcaaaac aagcaacagt attaacctt actaccgcac tgctggcagg    1020
aggcgcaact caagcgtttg cgaaagaaac gaaccaaaag ccatataagg aaacatacgg    1080
catttcccat attacacgcc atgatatgct gcaaatccct gaacagcaaa aaatgaaaa    1140 atatcaagtt cctgagttcg attcgtccac aattaaaaat atctcttctg caaaaggcct    1200
ggacgtttgg gacagctggc cattacaaaa cgctgacggc actgtcgcaa actatcacgg    1260
ctaccacatc gtctttgcat tagccggaga tcctaaaaat gcggatgaca catcgattta    1320
catgttctat caaaaagtcg gcgaaacttc tattgacagc tggaaaaacg ctggccgcgt    1380 cttttaaagac agcgacaaat tcgatgcaaa tgattctatc ctaaaagacc aaacacaaga    1440
atggtcaggt tcagccacat ttacatctga cggaaaaatc cgtttattct acactgattt    1500
ctccggtaaa cattacggca acaaacact gacaactgca caagttaacg tatcagcatc    1560
agacagctct ttgaacatca acggtgtaga ggattataaa tcaatctttg acggtgacgg    1620
aaaaacgtat caaaatgtac agcagttcat cgatgaaggc aactcagct caggcgacaa    1680 ccatacgctg agagatcctc actacgtaga agataaaggc cacaaatact tagtatttga    1740
agcaaacact ggaactgaag atggctacca aggcgaagaa tctttatta acaaagcata    1800 ctatggcaaa agcacatcat tcttccgtca agaaagtcaa aaacttctgc aaagcgataa    1860
aaaacgcacg gctgagttag caaacggcgc tctcggtatg attgagctaa acgatgatta    1920
cacactgaaa aaagtgatga aaccgctgat tgcatctaac acagtaacag atgaaattga    1980
acgcgcgaac gtcttaaa tgaacggcaa atggtatctg ttcactgact cccgcggatc    2040
aaaaatgacg attgacggca ttacgtctaa cgatatttac atgcttggtt atgtttctaa    2100
ttctttaact ggcccataca agccgctgaa caaaactggc cttgtgttaa aaatggatct    2160
tgatcctaac gatgtaacct ttacttactc acacttcgct gtacctcaag cgaaaggaaa    2220
caatgtcgtg attacaagct atatgacaaa cagaggattc tacgcagaca aacaatcaac    2280
gtttgcgccc agcttcctgc tgaacatcaa aggcaagaaa acatctgttg tcaaagacag    2340
catccttgaa caaggacaat taacagttaa caaataaaaa cgcaaaagaa aatgccgata    2400
tcctattggc attttctttt atttcttatc aacataaagg tgaatcccat atgaactata    2460
taaaagcagg caaatggcta accgtattcc taaccttttg gtaatgactc aacttattg    2520 atagtgtttt atgttcagat aatgcccgat gactttgtca tgcagctcca ccgatttga    2580 gaacgacagc gacttccgtc ccagccgtgc caggtgctgc ctcagattca ggttatgccg    2640
ctcaattcgc tgcgtatatc gcttgctgat tacgtgcagc tttcccttca ggcgggattc    2700
atacagcggc cagccatccg tcatccatat caccacgtca aagggtgaca gcaggctcat    2760
aagacgcccc agcgtcgcca tagtgcgttc accgaatacg tgcgcaacaa ccgtcttccg    2820
gagactgtca tacgcgtaaa acagccacgc tggcgcgat ttagccccga catagcccca    2880
ctgttcgtcc atttccgcgc agacgatgac gtcactgccc ggctgtatgc gcgaggttac    2940
cgactgcggc ctgagttttt taagtgacgt aaaatcgtgt tgaggccaac gcccataatg    3000
cgggctgttg cccggcatcc aacgccattc atggccatat caatgatttt ctggtgcgta    3060
```

```
ccgggttgag aagcggtgta agtgaactgc atgaattccc gggagagctc gatatcgcat    3120
gcggtacctc tagaagaagc ttcaaccaaa acatcgccat cgacctggaa ggcaaaaagt    3180
tgctcgattg acattatgcg caacaacacc cgctgttgcg caacgccgcc cctgttcggg    3240
cggcgttatc gccagcgaca tcgtaaacag cgtaataaca aaccgttgtg gatctgcaca    3300
gatgtctttt gaaacagggt tttcattttc cttttttgta aatttcagcg tataatgcgc    3360
gccaattgtc tcttgaatgg tttcagcgca ttggactgta aaactcaacg actaaaatta    3420
tccccttccc gttgggctga aacgcgagca cacattcctc tgcacgctct ttcgatgtca    3480
cctatcctta gagcgaggca tcatcacttt agcaacacag gcttagcttc cgggccgtgc    3540
gcgcccgaag ccagatttcc atatcctcct caacttaaag actaagactg tctaattgtt    3600
gtgtgaatta atttgtttaa aaagcgccc ttccggcgct tttttattt aatcgatagc     3660 cactattaat aaaaaaatca aatcggattt tactatctaa ttgcggatta tctaagaaga    3720
atccgatgga agccccctgt tttctttcgg ttttttaggg actttcatgc atttcgatgc    3780
ttctttgagc gaacgatcaa aaataagtgc attcccatca aaaaaatatt ctcaacataa    3840
aaaagtttgt gtaatacttg taacgctaca tggagattaa ctcaatctag agggtattaa    3900
taatgaatcg tactaaactg gtactgggcg cggtaatcct gggttctact ctgctggctg    3960
gttgctccag caacgctaaa atcgatcagc tgtcttctga cgttcagact ctgaacgcta    4020
aagttgacca gctgagcaac gagaattccg gatgagcatt catcaggcgg caagaatgt     4080 gaataaaggc cggataaaac ttgtgcttat ttttctttac ggtctttaaa aaggccgtaa    4140
tatccagctg aacggtctgg ttataggtac attgagcaac tgactgaaat gcctcaaaat    4200
gttctttacg atgccattgg gatatatcaa cggtggtata ccagtgatt ttttctcca     4260 ttttagcttc cttagctcct gaaaatctcg ataactcaaa aaatacgccc ggtagtgatc    4320
ttatttcatt atggtgaaag ttggaacctc ttacgtgccg atcaacgtct cattttcgcc    4380
aaaagttggc ccagggcttc ccggtatcaa caggacacc aggatttatt tattctgcga     4440
agtgatcttc cgtcacaggt attagggccc gatcctttt gtccggtgtt gggttgaagg     4500
tgaagccggt cggggccgca gcgggggccg gcttttcagc cttgcccccc tgcttcggcc    4560
gccgtggctc cggcgtcttg ggtgccggcg cgggttccgc agccttggcc tgcggtgcgg    4620
gcacatcggg gggcttggcc ttgatgtgcc gcctggcgtg cgagcggaac gtctcgtagg    4680
agaacttgac cttccccgtt tcccgcatgt gctcccaaat ggtgacgagc gcatagccgg    4740
acgctaacgc cgcctcgaca tccgccctca ccgccaggaa cgcaaccgca gcctcatcac    4800
gccggcgctt cttggccgcg cgggattcaa cccactcggc cagctcgtcg gtgtagctct    4860
ttggcatcgt ctctcgcctg tccctcagt tcagtaattt cctgcatttg cctgtttcca     4920
gtcggtagat attccacaaa acagcaggga agcagcgctt ttccgctgca taaccctgct    4980
tcggggtcat tatagcgatt ttttcggtat atccatcctt tttcgcacga tatacaggat    5040
tttgccaaag ggttcgtgta gactttcctt ggtgtatcca acggcgtcag ccgggcagga    5100
taggtgaagt aggcccaccc gcgagcgggt gttccttctt cactgtccct tattcgcacc    5160
tggcggtgct caacgggaat cctgctctgc gaggctggcc ggctaccgcc ggcgtaacag    5220
atgagggcaa gcggatggct gatgaaacca agccaaccag gaagggcagc ccacctatca    5280
aggtgtactg ccttccagac gaacgaagag cgattgagga aaaggcgcg gcggccggca    5340 tgagcctgtc ggcctacctg ctggccgtcg gccaggcta caaaatcacg ggcgtcgtgg     5400
actatgagca cgtccgcgag ctggcccgca tcaatggcga cctgggccgc ctgggcggcc    5460
```

```
tgctgaaact ctggctcacc gacgacccgc gcacggcgcg gttcggtgat gccacgatcc   5520
tcgccctgct ggcgaagatc gaagagaagc aggacgagct tggcaaggtc atgatgggcg   5580
tggtccgccc gagggcagag ccatgacttt tttagccgct aaaacggccg ggggtgcgc    5640 gtgattgcca agcacgtccc catgcgctcc atcaagaaga cgacttcgc ggagctggtg    5700 aagtacatca ccgacgagca aggcaagacc gagcgcctgg gtcacgtgcg cgtcacgaac   5760
tgcgaggcaa acaccctgcc cgctgtcatg gccgaggtga tggcgaccca gcacggcaac   5820
acccgttccg aggccgacaa gacctatcac ctgctggtta gcttccgcgc gggagagaag   5880
cccgacgcgg agacgttgcg cgcgattgag gaccgcatct cgctgggct tggcttcgcc    5940 gagcatcagc gcgtcagtgc cgtgcatcac gacaccgaca acctgcacat ccatatcgcc   6000
atcaacaaga ttcacccgac ccgaaacacc atccatgagc cgtatcgggc ctaccgcgcc   6060
ctcgctgacc tctgcgcgac gctcgaacgg gactacgggc ttgagcgtga caatcacgaa   6120
acgcggcagc gcgtttccga gaaccg                                        6146
```

<210> SEQ ID NO 5
<211> LENGTH: 32
<212> TYPE: DNA
<213> ORGANISM: Artificial Sequence
<220> FEATURE:
<223> OTHER INFORMATION: Synthetic- pstG Primer 1 for construction of
      pK4960 plasmid

<400> SEQUENCE: 5

```
ccaagcttcg cggtaaagag aaccagcctg cg                                   32
```

<210> SEQ ID NO 6
<211> LENGTH: 95
<212> TYPE: DNA
<213> ORGANISM: Artificial Sequence
<220> FEATURE:
<223> OTHER INFORMATION: Synthetic- pstG Primer 2 for construction of
      pK4960 plasmid

<400> SEQUENCE: 6

```
tggttcgtcg taacaggtgc ctacgcatct acacattata cgagccggat gattaattgt   60
caacagctca tttcagaata attgagagtg ctcct                               95
```

<210> SEQ ID NO 7
<211> LENGTH: 119
<212> TYPE: DNA
<213> ORGANISM: Artificial Sequence
<220> FEATURE:
<223> OTHER INFORMATION: Synthetic- pstG Primer 3 for construction of
      pK4960 plasmid

<400> SEQUENCE: 7

```
ctgttacgac gaaccacaca ggaaacagac catgtttaag aatgcatttg ctaacctgca   60
aaaggtcggt aaatcgctga tgctgccggt atccgtactc cctatcgcag gtatcctgc    119
```

<210> SEQ ID NO 8
<211> LENGTH: 32
<212> TYPE: DNA
<213> ORGANISM: Artificial Sequence
<220> FEATURE:
<223> OTHER INFORMATION: Synthetic- pstG Primer 4 for construction of
      pK4960 plasmid <210> SEQ ID NO 9
<211> LENGTH: 32
<212> TYPE: DNA
<213> ORGANISM: Artificial Sequence
<220> FEATURE:
<223> OTHER INFORMATION: Synthetic- pykA Primer 1 for construction of pK4961 plasmid

<400> SEQUENCE: 9
ccaagcttat ttcgcatact ggcagaacca ag             32

<210> SEQ ID NO 10
<211> LENGTH: 24
<212> TYPE: DNA
<213> ORGANISM: Artificial Sequence
<220> FEATURE:
<223> OTHER INFORMATION: Synthetic- pykA Primer 2 for construction of pK4961 plasmid

<400> SEQUENCE: 10
gtaatactcc gttgactaaa acaa                       24

<210> SEQ ID NO 11
<211> LENGTH: 24
<212> TYPE: DNA
<213> ORGANISM: Artificial Sequence
<220> FEATURE:
<223> OTHER INFORMATION: pykA Primer 3 for construction of pK4961 plasmid

<400> SEQUENCE: 11
aactccccca cgcctgttca tcag                       24

<210> SEQ ID NO 12
<211> LENGTH: 32
<212> TYPE: DNA
<213> ORGANISM: Artificial Sequence
<220> FEATURE:
<223> OTHER INFORMATION: pykA Primer 4 for construction of pK4961 plasmid

<400> SEQUENCE: 12
gggaattccg tcagggctac tggggttact ac             32

<210> SEQ ID NO 13
<211> LENGTH: 32
<212> TYPE: DNA
<213> ORGANISM: Artificial Sequence
<220> FEATURE:
<223> OTHER INFORMATION: Synthetic- pykF Primer 1 for construction of pK4962 plasmid

<400> SEQUENCE: 13
ccaagcttca accaaaacat cgccatcgac ct             32

<210> SEQ ID NO 14
<211> LENGTH: 24
<212> TYPE: DNA
<213> ORGANISM: Artificial Sequence
<220> FEATURE:
<223> OTHER INFORMATION: pykF Primer 2 for construction of pK4962 plasmid

```
<400> SEQUENCE: 14
gacagtctta gtctttaagt tgag                                           24

<210> SEQ ID NO 15
<211> LENGTH: 24
<212> TYPE: DNA
<213> ORGANISM: Artificial Sequence
<220> FEATURE:
<223> OTHER INFORMATION: Synthetic- pykF Primer 3 for construction of
      pK4962 plasmid

<400> SEQUENCE: 15
taattgttgt gtgaattaat ttgt                                           24

<210> SEQ ID NO 16
<211> LENGTH: 32
<212> TYPE: DNA
<213> ORGANISM: Artificial Sequence
<220> FEATURE:
<223> OTHER INFORMATION: Synthetic- pykF Primer 4 for construction of
      pK4962 plasmid

<400> SEQUENCE: 16
gggaattctc gttgctcagc tggtcaactt ta                                  32
```